(12) United States Patent
de Fougerolles et al.

(10) Patent No.: US 8,334,273 B2
(45) Date of Patent: Dec. 18, 2012

(54) COMPOSITIONS AND METHODS FOR INHIBITING EXPRESSION OF FACTOR VII GENE

(75) Inventors: Antonin de Fougerolles, Cambridge, MA (US); Tatiana Novobrantseva, Wellesley, MA (US); Akin Akinc, Needham, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 110 days.

(21) Appl. No.: 12/970,673

(22) Filed: Dec. 16, 2010

(65) Prior Publication Data

US 2012/0208860 A1    Aug. 16, 2012

Related U.S. Application Data

(63) Continuation of application No. 12/331,708, filed on Dec. 10, 2008, now Pat. No. 7,871,985.

(60) Provisional application No. 61/012,670, filed on Dec. 10, 2007, provisional application No. 61/014,879, filed on Dec. 19, 2007.

(51) Int. Cl.
| | | |
|---|---|---|
| A61K 31/70 | (2006.01) | |
| C07H 21/02 | (2006.01) | |
| C07H 21/04 | (2006.01) | |
| C12Q 1/68 | (2006.01) | |
| C12P 19/34 | (2006.01) | |

(52) U.S. Cl. ...... 514/44 A; 536/24.5; 435/6.1; 435/91.1; 435/325; 435/375

(58) Field of Classification Search .................. 514/44; 435/6, 91.1, 325, 375; 536/24.5
See application file for complete search history.

(56) References Cited

U.S. PATENT DOCUMENTS

| | | |
|---|---|---|
| 2003/0143732 A1 | 7/2003 | Fosnaugh et al. |
| 2004/0259247 A1 | 12/2004 | Tuschl et al. |
| 2007/0004664 A1 | 1/2007 | McSwiggen et al. |
| 2007/0031844 A1 | 2/2007 | Khvorova et al. |

FOREIGN PATENT DOCUMENTS

| | | |
|---|---|---|
| WO | WO 2004/080406 | 9/2004 |
| WO | WO 2004/090108 | 10/2004 |

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, pp. 494-498, vol. 411.
Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.
Elbashir, S., et al., "RNA Interference is Mediated by 21 -and 22 Nucleotide RNAs," Genes & Development, 2001, pp. 188-200, vol. 15.

(Continued)

*Primary Examiner* — Terra Cotta Gibbs
(74) *Attorney, Agent, or Firm* — Fenwick & West LLP

(57) ABSTRACT

The invention relates to a double-stranded ribonucleic acid (dsRNA) for inhibiting the expression of the Factor VII gene.

25 Claims, 17 Drawing Sheets

OTHER PUBLICATIONS

Fire, A., "RNA-triggered Gene Silencing," Trends in Genetics, Sep. 1999, pp. 358-363, vol. 15, No. 9.

Fire, A., et al., "Potent and Specific Genetic Interference By Double Stranded RNA in Caenorhabditis elegans," Nature, Feb. 19, 1998, pp. 806-811, vol. 391.

Robbins, M., et al., "Stable expression of shRNAs in human CD34+progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation By Double-Stranded RNA In Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

```
   1 agtcccatgg ggaatgtcaa caggcagggg cagcactgca gagatttcat catggtctcc
  61 caggccctca ggctcctctg ccttctgctt gggcttcagg gctgcctggc tgcaggcggg
 121 gtcgctaagg cctcaggagg agaaacacgg gacatgccgt ggaagccggg gcctcacaga
 181 gtcttcgtaa cccaggagga agcccacggc gtcctgcacc ggcgccggcg cgccaacgcg
 241 ttcctggagg agctgcggcc gggctccctg gagagggagt gcaaggagga gcagtgctcc
 301 ttcgaggagg cccgggagat cttcaaggac gcggagagga cgaagctgtt ctggatttct
 361 tacagtgatg ggaccagtg tgcctcaagt ccatgccaga atggggctc ctgcaaggac
 421 cagctccagt cctatatctg cttctgcctc cctgccttcg agggccggaa ctgtgagacg
 481 cacaaggatg accagctgat ctgtgtgaac gagaacggcg gctgtgagca gtactgcagt
 541 gaccacacgg gcaccaagcg ctcctgtcgg tgccacgagg ggtactctct gctggcagac
 601 ggggtgtcct gcacacccac agttgaatat ccatgtggaa aaatacctat tctagaaaaa
 661 agaaatgcca gcaaacccca aggccgaatt gtgggggca aggtgtgccc caaggggag
 721 tgtccatggc aggtcctgtt gttggtgaat ggagctcagt tgtgtggggg gaccctgatc
 781 aacaccatct gggtggtctc cgcggcccac tgtttcgaca aaatcaagaa ctggaggaac
 841 ctgatcgcgg tgctgggcga gcacgacctc agcgagcacg acggggatga gcagagccgg
 901 cgggtggcgc aggtcatcat ccccagcacg tacgtcccgg gcaccaccaa ccacgacatc
 961 gcgctgctcc gcctgcacca gccgtggtc ctcactgacc atgtggtgcc cctctgcctg
1021 cccgaacgga cgttctctga gaggacgctg gccttcgtgc gcttctcatt ggtcagcggc
1081 tggggccagc tgctggaccg tggcgccacg gccctggagc tcatggtcct caacgtgccc
1141 cggctgatga cccaggactg cctgcagcag tcacggaagg tgggagactc cccaaatatc
1201 acggagtaca tgttctgtgc cggctactcg gatggcagca aggactcctg caaggggac
1261 agtggaggcc cacatgccac ccactaccgg ggcacgtggt acctgacggg catcgtcagc
1321 tggggccagg gctgcgcaac cgtgggccac tttggggtgt acaccagggt ctcccagtac
1381 atcgagtggc tgcaaaagct catgcgctca gagccacgcc aggagtcct cctgcgagcc
1441 ccatttccct agcccagcag ccctggcctg tggagagaaa gccaaggctg cgtcgaactg
1501 tcctggcacc aaatcccata tattcttctg cagttaatgg ggtagaggag ggcatgggag
1561 ggagggagag gtggggaggg agacagagac agaaacagag agacagag acagagagag
1621 actgagggag agactctgag gacatggaga gagactcaaa gagactccaa gattcaaaga
1681 gactaataga gacacagaga tggaatagaa aagatgagag gcagaggcag acaggcgctg
1741 gacagagggg caggggagtg ccaaggttgt cctggaggca gacagcccag ctgagcctcc
1801 ttacctccct tcagccaagc ccacctgcac gtgatctgct ggcctcaggc tgctgctctg
1861 ccttcattgc tggagacagt agaggcatga acacacatgg atgcacacac acacacgcca
1921 atgcacacac acagagatat gcacacacac ggatgcacac acagatggtc acacagagat
1981 acgcaaacac accgatgcac acgcacatag agatatgcac acagatgcac acacagat
```

FIG. 7A

```
2041 atacacatgg atgcacgcac atgccaatgc acgcacacat cagtgcacac ggatgcacag
2101 agatatgcac acaccgatgt gcgcacacac agatatgcac acacatggat gagcacacac
2161 acaccaatgc gcacacacac cgatgtacac acacagatgc acacacagat gcacacacac
2221 cgatgctgac tccatgtgtg ctgtcctctg aaggcggttg tttagctctc acttttctgg
2281 ttcttatcca ttatcatctt cacttcagac aattcagaag catcaccatg catggtggcg
2341 aatgccccca aactctcccc caaatgtatt tctcccttcg ctgggtgccg ggctgcacag
2401 actattcccc acctgcttcc cagcttcaca ataaacggct gcgtctcctc cgcacacctg
2461 tggtgcctgc cacccactgg gttgcccatg attcattttt ggagcccccg gtgctcatcc
2521 tctgagatgc tcttttcttt cacaattttc aacatcactg aaatgaaccc tcacatggaa
2581 gctattttt aaaaacaaaa gctgtttgat agatgtttga ggctgtagct cccaggatcc
2641 tgtggaattg gatgttctct ccctgccaca gcccttgtca atgatatttc acagagaccc
2701 tgggagcacc tgctcaagag tcagggacac acgcatcact aaatgcaagt tcccaggccc
2761 tggctgcagt gggaggacct ggcaagctgc actcttgctg agtccccagg gtggtggaag
2821 aagaatgaga aacacatgaa cagagaaatg gggaggtgac aaacagtgcc cccactcaga
2881 ctccggcaag cacggctcag agagtggact cgatgccatc cctgcagggc cgtcctgggc
2941 accactggca ctcacagcag caaggtgggc accattggca ctcacagcag caaggcaggc
3001 accagcaacc cacctcgggg gcactcaggc atcatctact tcagagcaga cagggtctat
3061 gaactacagc cgtgggctgc ttccaaggca ccctgctctt gtaaataaag ttttatggga
3121 acacaaaaaa aaaaaaaaa a
```

FIG. 7B

```
   1 agtcccatgg ggaatgtcaa caggcagggg cagcactgca gagatttcat catggtctcc
  61 caggccctca ggctcctctg ccttctgctt gggcttcagg gctgcctggc tgcagtcttc
 121 gtaacccagg aggaagccca cggcgtcctg caccggcgcc ggcgcgccaa cgcgttcctg
 181 gaggagctgc ggccgggctc cctggagagg gagtgcaagg aggagcagtg ctccttcgag
 241 gaggcccggg agatcttcaa ggacgcggag aggacgaagc tgttctggat ttcttacagt
 301 gatggggacc agtgtgcctc aagtccatgc cagaatgggg gctcctgcaa ggaccagctc
 361 cagtcctata tctgcttctg cctccctgcc ttcgagggcc ggaactgtga gacgcacaag
 421 gatgaccagc tgatctgtgt gaacgagaac ggcggctgtg agcagtactg cagtgaccac
 481 acgggcacca agcgctcctg tcggtgccac gagggtact ctctgctggc agacggggtg
 541 tcctgcacac ccacagttga atatccatgt ggaaaaatac ctattctaga aaaagaaat
 601 gccagcaaac cccaaggccg aattgtgggg ggcaaggtgt gccccaaagg ggagtgtcca
 661 tggcaggtcc tgttgttggt gaatggagct cagttgtgtg gggggaccct gatcaacacc
 721 atctgggtgg tctccgcggc ccactgtttc gacaaaatca gaactggag gaacctgatc
 781 gcggtgctgg gcgagcacga cctcagcgag cacgacgggg atgagcagag ccggcgggtg
 841 gcgcaggtca tcatcccag cacgtacgtc ccgggcacca ccaaccacga catcgcgctg
 901 ctccgcctgc accagcccgt ggtcctcact gaccatgtgg tgccctctg cctgcccgaa
 961 cggacgttct ctgagaggac gctggccttc gtgcgcttct cattggtcag cggctgggc
1021 cagctgctgg accgtggcgc cacggccctg gagctcatgg tcctcaacgt gccccggctg
1081 atgacccagg actgcctgca gcagtcacgg aaggtgggag actccccaaa tatcacggag
1141 tacatgttct gtgccggcta ctcggatggc agcaaggact cctgcaaggg ggacagtgga
1201 ggcccacatg ccacccacta ccggggcacg tggtacctga cgggcatcgt cagctgggc
1261 cagggctgcg caaccgtggg ccactttggg gtgtacacca gggtctccca gtacatcgag
1321 tggctgcaaa agctcatgcg ctcagagcca cgcccaggag tcctcctgcg agccccattt
1381 ccctagccca gcagccctgg cctgtggaga gaaagccaag gctgcgtcga actgtcctgg
1441 caccaaatcc catatattct tctgcagtta atggggtaga ggagggcatg ggagggaggg
1501 agaggtgggg agggagacag agacagaaac agagagagac agagacagag agagactgag
1561 ggagagactc tgaggacatg gagagagact caaagagact ccaagattca aagagactaa
1621 tagagacaca gagatggaat agaaaagatg agaggcagag cagacaggc gctggacaga
1681 gggcagggg agtgccaagg ttgtcctgga ggcagacagc ccagctgagc ctccttacct
1741 cccttcagcc aagcccacct gcacgtgatc tgctggcctc aggctgctgc tctgccttca
1801 ttgctggaga cagtagaggc atgaacacac atggatgcac acacacacac gccaatgcac
1861 acacacagag atatgcacac acacggatgc acacacagat ggtcacacag agatacgcaa
1921 acacaccgat gcacacgcac atagagatat gcacacacag atgcacacac agatatacac
1981 atggatgcac gcacatgcca atgcacgcac acatcagtgc acacggatgc acagagatat
```

FIG. 8A

```
2041 gcacacaccg atgtgcgcac acacagatat gcacacacat ggatgagcac acacacacca
2101 atgcgcacac acaccgatgt acacacacag atgcacacac agatgcacac acaccgatgc
2161 tgactccatg tgtgctgtcc tctgaaggcg gttgtttagc tctcactttt ctggttctta
2221 tccattatca tcttcacttc agacaattca gaagcatcac catgcatggt ggcgaatgcc
2281 cccaaactct cccccaaatg tatttctccc ttcgctgggt gccgggctgc acagactatt
2341 ccccacctgc ttcccagctt cacaataaac ggctgcgtct cctccgcaca cctgtggtgc
2401 ctgccaccca ctgggttgcc catgattcat ttttggagcc cccggtgctc atcctctgag
2461 atgctctttt ctttcacaat tttcaacatc actgaaatga accctcacat ggaagctatt
2521 ttttaaaaac aaaagctgtt tgatagatgt ttgaggctgt agctccagg atcctgtgga
2581 attggatgtt ctctccctgc cacagccctt gtcaatgata tttcacagag accctgggag
2641 cacctgctca agagtcaggg acacacgcat cactaaatgc aagttcccag gccctggctg
2701 cagtgggagg acctggcaag ctgcactctt gctgagtccc cagggtggtg aagaagaat
2761 gagaaacaca tgaacagaga aatggggagg tgacaaacag tgcccccact cagactccgg
2821 caagcacggc tcagagagtg gactcgatgc catccctgca gggccgtcct gggcaccact
2881 ggcactcaca gcagcaaggt gggcaccatt ggcactcaca gcagcaaggc aggcaccagc
2941 aacccacctc ggggcactc aggcatcatc tacttcagag cagacagggt ctatgaacta
3001 cagccgtggg ctgcttccaa ggcaccctgc tcttgtaaat aaagttttat gggaacacaa
3061 aaaaaaaaaa aaaaa
```

FIG. 8B

```
   1 ggccattacg gccggggatt tcatcatggt ctctcgagcc ctcgggctcc tctgccttct
  61 gcttgggctt cagggctgtc tggctgcagc caccttcctg ccccaggcgg ggtcgctgag
 121 gcctcaggag gagaaaacac aggacctgct gtggaagcca gggcctcaca gagtcttcgt
 181 aacccaggag gaagcccatg gcgtcctgca caggcagcgg cgcgccaact cgttcctgga
 241 ggagctgcgg ccgggctccc tggagaggga gtgcaaggag gagcaatgct ccttcgagga
 301 ggcccgggag atcttcaagg acctggagag gacgaagctg ttctggattt cttacagtga
 361 tggggaccag tgtgcctcaa atccgtgcca gaatgggggc tcctgcaagg accagctcca
 421 gtcctatatc tgcttctgcc tcccttcctt cgagggccgg aactgtgaga gaacaagga
 481 tgaccagctg atctgcgtga cgagaacgg cggctgtgag cagtactgca gtgaccacgc
 541 gggtgccaag cgctcctgtt ggtgccacga ggggtactcg ctgctggcag acggggtgtc
 601 ctgcatgccc acagttgaat atccatgtgg aaaatacct attctggaaa aagaaatgc
 661 cagcaaaccc caaggccgaa ttgtcggggg cagggtgtgc cccaaggggg agtgtccatg
 721 gcaggtcctg ttgttggtga atggagctca gctgtgtgga gggaccctga taaacaccat
 781 ctgggtggtc tctgcggccc actgttttga caaaatcaag agctggagga acttgaccgc
 841 ggtgctgggc gagcacgacc tcagcgagca cgaaggggat gagcagagcc ggcgggtggc
 901 gcaggtcatc atccccagca cgtatgtcct gggcgccacc aaccacgaca tcgcgctgct
 961 ccgcctgcag cagcccgtgg tcctcactga ccatgtggtg ccctctgcc tgcccgaacg
1021 gatgttctcc gagaggacgc tggccttcgt gcgcttctcg ttggtcagcg gctgggtca
1081 gctgctggac cgtggtgcca cagccctgga gctcatggcc ctcaacgtgc cccggctgat
1141 gacccaggac tgcctgcagc agtcacagaa ggcagaagcc tccccgaata tcacggagta
1201 catgttctgt gccggctact cggacggcag cagggactcc tgcaagggg acagtggagg
1261 cccacacgcc acccgctacc ggggcacgtg gtacctgaca ggcatcgtca gctgggggcca
1321 gggctgcgca gccgtgggcc acttcgggt gtacaccagg gtctcccagt acatcgagtg
1381 gctgcaaaag ctcatgcact cagagccacg cccaggcgtc ctcctgcgag ccccatttcc
1441 ctagcctagc agccctgccc cctggagaga aagccaaggc tgtgtagaac tgttctggca
1501 caaaatccca tcgattcttc tgcagttcat ggggtagagg agggcatggg agggaggag
1561 aggtggggag ggagacagag acagaaacag agagacaaag agacagggag agactgaggg
1621 agaggttctg aggacatgga gagactcaaa gagactccaa gattcaaaga gcctaataga
1681 gacacagaga aggaatcgaa aagatgagat gcagaggcag acaggcgctg gacagagggg
1741 caggggaatg ccgcggttgt cctggaggca gacagcccag ctgagcctcc ttatctctct
1801 tcagccaagc ccacctgccc gtgatctgct ggcctcaggc tgctgttctg ccttcattgc
1861 tggagacact agaggcatgt acacatgtgg atgcatacac acaccaat gcacacacag
1921 agatatgcac acacagaggg tcacacagag atatgcaaac acactgatac acacacatac
1981 agagatatgc acatacacgg atgcatatac acagatatgc ccacacacag atgcgtgcac
```

FIG. 9A

```
2041 accacaccaa tgcacgcaca cactaatgca cccacacgga tgcagagaga tatgcacaca
2101 ccgatgtgca catacacaga tatgcacaca catggatgag tgcacacaca ctaatgtaca
2161 cacacagata tgcacacacg gatgcacaca caccgatgct gactccatgt gtgctgtcct
2221 ccaaaggcgg ttgtttagct ctcactttc tcgttcttat ccattatcat cttcatttca
2281 gacaattcag aagcatcacc atgcatgttg gcaaatgccc caaactctcc cccaaatgtg
2341 ccgggctgca caggccgttc cccaccggct tcccaacttc acaataaatg gctgcatctc
2401 ctccgcaaaa aaaaaaaaaa aaaa
```

FIG. 9B

```
  1 cgagcacgaa ggggatgagc agagccggcg ggtggcgcag gtcatcatcc ccagcacgta
 61 tgtcctgggc gccaccaacc acgacatcgc gctgctccgc ctgcagcagc ccgtggtcct
121 cactgaccat gtggtgcccc tctgcctgcc cgaacggatg ttctccgaga ggacgctggc
181 cttcgtgcgc ttctcattgg tcagcggctg gggtcagctg ctggaccgtg gtgccacagc
241 cctggagctc atggccctca acgtgccccg gctgatgacc caggactgcc tgcagcagtc
301 acagaaggca gaagcctccc cgaatatcac ggagtacatg ttctgtgccg gctactcgga
361 cggcagcagg gactcctgca aggggacag tggaggccca cacgccaccc gctaccgggg
421 cacgtggtac ctgacaggca tcgtcagctg gggccagggc tgcgcagccg tgggccac
```

FIG. 10

```
  1 ATGGTCTCTCGAGCCCTCGGGCTCCTCTGCCTTCTGCTTGGGCTTCAGGGCTGTCTGGCT
  1 ATGGTCTCTCGAGCCCTCGGGCTCCTCTGCCTTCTGCTTGGGCTTCAGGGCTGTCTGGCT
  1 -M--V--S--R--A--L--G--L--L--C--L--L--L--G--L--Q--G--C--L--A-

61 GCAGGCGGGGTCGCTGAGGCCTCAGGAGGAGAACAGGACCTGCTGTGGAAGCCAGGGCCT
 61 GCAGGCGGGGTCGCTGAGGCCTCAGGAGGAGAACAGGACCTGCTGTGGAAGCCAGGGCCT
 21 -A--G--G--V--A--E--A--S--G--G--E--Q--D--L--L--W--K--P--G--P-

121 CACAGAGGACGCCTCACACAAGACACCTCACATGGTGCACTTCACACTCACAGGTCACCT
121 CACAGAGGACGCCTCACACAAGACACCTCACATGGTGCACTTCACACTCACAGGTCACCT
 41 -H--R--G--R--L--T--Q--D--T--S--H--G--A--L--H--T--H--R--S--P-

181 CACATTCGACACCTCACACTGAGCACACTTCACACTCGGGACACCTCACACTCAGGTTCC
181 CACATTCGACACCTCACACTGAGCACACTTCACACTCGGGACACCTCACACTCAGGTTCC
 61 -H--I--R--H--L--T--L--S--T--L--H--T--R--D--T--S--H--S--G--S-

241 CCAACCCCAGCTCGTGGTTTGTCCAGTGCTCACCGTTGGAAGCTGTTCTGGATTTCTTAC
241 CCAACCCCAGCTCGTGGTTTGTCCAGTGCTCACCGTTGGAAGCTGTTCTGGATTTCTTAC
 81 -P--T--P--A--R--G--L--S--S--A--H--R--W--K--L--F--W--I--S--Y-

301 AGTGATGGGGACCAGTGTGCCTCAAATCCGTGCCAGAATGGGGGCTCCTGCAAGGACCAG
301 AGTGATGGGGACCAGTGTGCCTCAAATCCGTGCCAGAATGGGGGCTCCTGCAAGGACCAG
101 -S--D--G--D--Q--C--A--S--N--P--C--Q--N--G--G--S--C--K--D--Q-

361 CTCCAGTCCTATATCTGCTTCTGCCTCCCTTCCTTCGAGGGCCGGAACTGTGAGAAGAAC
361 CTCCAGTCCTATATCTGCTTCTGCCTCCCTTCCTTCGAGGGCCGGAACTGTGAGAAGAAC
121 -L--Q--S--Y--I--C--F--C--L--P--S--F--E--G--R--N--C--E--K--N-

421 AAGGATGACCAGCTGATCTGCGTGAACGAGAACGGCGGCTGTGAGCAGTACTGCAGTGAC
421 AAGGATGACCAGCTGATCTGCGTGAACGAGAACGGCGGCTGTGAGCAGTACTGCAGTGAC
141 -K--D--D--Q--L--I--C--V--N--E--N--G--G--C--E--Q--Y--C--S--D-

481 CACGCGGGTGCCAAGCGCTCCTGTTGGTGCCACGAGGGGTACTCGCTGCTGGCAGACGGG
481 CACGCGGGTGCCAAGCGCTCCTGTTGGTGCCACGAGGGGTACTCGCTGCTGGCAGACGGG
161 -H--A--G--A--K--R--S--C--W--C--H--E--G--Y--S--L--L--A--D--G-

541 GTGTCCTGCATGCCCACAGTTGAATATCCATGTGGAAAAATACCTATTCTGGAAAAAAGA
541 GTGTCCTGCATGCCCACAGTTGAATATCCATGTGGAAAAATACCTATTCTGGAAAAAAGA
181 -V--S--C--M--P--T--V--E--Y--P--C--G--K--I--P--I--L--E--K--R-
```

FIG. 11A

```
601 AATGCCAGCAAACCCCAAGGCCGAATTGTCGGGGGCAGGGTGTGCCCCAAAGGGGAGTGT
601 AATGCCAGCAAACCCCAAGGCCGAATTGTCGGGGGCAGGGTGTGCCCCAAAGGGGAGTGT
201 -N--A--S--K--P--Q--G--R--I--V--G--G--R--V--C--P--K--G--E--C-

661 CCATGGCAGGTCCTGTTGTTGGTGAATGGAGCTCAGCTGTGTGGAGGGACCCTGATAAAC
661 CCATGGCAGGTCCTGTTGTTGGTGAATGGAGCTCAGCTGTGTGGAGGGACCCTGATAAAC
221 -P--W--Q--V--L--L--V--N--G--A--Q--L--C--G--G--T--L--I--N-

721 ACCATCTGGGTGGTCTCTGCGGCCCACTGTTTCGACAAAATCAAGAGCTGGAGGAACTTG
721 ACCATCTGGGTGGTCTCTGCGGCCCACTGTTTCGACAAAATCAAGAGCTGGAGGAACTTG
241 -T--I--W--V--V--S--A--A--H--C--F--D--K--I--K--S--W--R--N--L-

781 ACCGCGGTGCTGGGCGAGCACGACCTCAGCGAGCACGAAGGGGATGAGCAGAGCCGGCGG
781 ACCGCGGTGCTGGGCGAGCACGACCTCAGCGAGCACGAAGGGGATGAGCAGAGCCGGCGG
261 -T--A--V--L--G--E--H--D--L--S--E--H--E--G--D--E--Q--S--R--R-

841 GTGGCGCAGGTCATCATCCCCAGCACGTATGTCCTGGGCGCCACCAACCACGACATCGCG
841 GTGGCGCAGGTCATCATCCCCAGCACGTATGTCCTGGGCGCCACCAACCACGACATCGCG
281 -V--A--Q--V--I--I--P--S--T--Y--V--L--G--A--T--N--H--D--I--A-

901 CTGCTCCGCCTGCAGCAGCCCGTGGTCCTCACTGACCATGTGGTGCCCCTCTGCCTGCCC
901 CTGCTCCGCCTGCAGCAGCCCGTGGTCCTCACTGACCATGTGGTGCCCCTCTGCCTGCCC
301 -L--L--R--L--Q--Q--P--V--V--L--T--D--H--V--V--P--L--C--L--P-

961 GAACGGACGTTCTCCGAGAGGACGCTGGCCTTCGTGCGCTTCTCGTTGGTCAGCGGCTGG
961 GAACGGACGTTCTCCGAGAGGACGCTGGCCTTCGTGCGCTTCTCGTTGGTCAGCGGCTGG
321 -E--R--T--F--S--E--R--T--L--A--F--V--R--F--S--L--V--S--G--W-

1021 GGTCAGCTGCTGGACCGTGGTGCCACAGCCCTGGAGCTCATGGCCCTCAACGTGCCCCGG
1021 GGTCAGCTGCTGGACCGTGGTGCCACAGCCCTGGAGCTCATGGCCCTCAACGTGCCCCGG
341 -G--Q--L--L--D--R--G--A--T--A--L--E--L--M--A--L--N--V--P--R-

1081 CTGATGACCCAGGACTGCCTGCAGCAGTCACAGAAGGCAGAAGCCTCCCCGAATATCACG
1081 CTGATGACCCAGGACTGCCTGCAGCAGTCACAGAAGGCAGAAGCCTCCCCGAATATCACG
361 -L--M--T--Q--D--C--L--Q--Q--S--Q--K--A--E--A--S--P--N--I--T-
```

FIG. 11B

```
1141 GAGTACATGTTCTGTGCCGGCTACTCGGACGGCAGCAGGGACTCCTGCAAGGGGGACAGT
1141 GAGTACATGTTCTGTGCCGGCTACTCGGACGGCAGCAGGGACTCCTGCAAGGGGGACAGT
 381 -E--Y--M--F--C--A--G--Y--S--D--G--S--R--D--S--C--K--G--D--S-

1201 GGAGGCCCACACGCCACCCGCTACCGGGGCACGTGGTACCTGACAGGCATCGTCAGCTGG
1201 GGAGGCCCACACGCCACCCGCTACCGGGGCACGTGGTACCTGACAGGCATCGTCAGCTGG
 401 -G--G--P--H--A--T--R--Y--R--G--T--W--Y--L--T--G--I--V--S--W-

1261 GGCCAGGGCTGCGCGGCCGTGGGCCACTTCGGGGTGTACACCAGGGTCTCCCAGTACATC
1261 GGCCAGGGCTGCGCGGCCGTGGGCCACTTCGGGGTGTACACCAGGGTCTCCCAGTACATC
 421 -G--Q--G--C--A--A--V--G--H--F--G--V--Y--T--R--V--S--Q--Y--I-

1321 GAGTGGCTGCAAAAGCTCATGCACTCAGAGCCACGCCCAGGCGTCCTCCTGCGAGCCCCA
1321 GAGTGGCTGCAAAAGCTCATGCACTCAGAGCCACGCCCAGGCGTCCTCCTGCGAGCCCCA
 441 -E--W--L--Q--K--L--M--H--S--E--P--R--P--G--V--L--L--R--A--P-

1381 TTTCCCTAG
1381 TTTCCCTAG
 461 -F--P--*-
```

FIG. 11C

```
ATGGTCTCTCGAGCCCTCGGGCTCCTCTGCCTTCTGCTTGGGCTTCAGGGCTGTCTGGCT
GCAGGACGCCTCACACAAGACACCTCACATGGTGCACTTCACACTCACAGGTCACCTCAC
ATTCGACACCTCACACTGAGCACACTTCACACTCGGGACACCTCACACTCAGGTTCCCCA
ACCCCAGCTCGTGGTTTGTCCAGTGCTCACCGTTGGAAGCTGTTCTGGATTTCTTACAGT
GATGGGGACCAGTGTGCCTCAAATCCGTGCCAGAATGGGGGCTCCTGCAAGGACCAGCTC
CAGTCCTATATCTGCTTCTGCCTCCCTTCCTTCGAGGGCCGGAACTGTGAGAAGAACAAG
GATGACCAGCTGATCTGCGTGAACGAGAACGGCGGCTGTGAGCAGTACTGCAGTGACCAC
GCGGGTGCCAAGCGCTCCTGTTGGTGCCACGAGGGGTACTCGCTGCTGGCAGACGGGGTG
TCCTGCATGCCCACAGTTGAATATCCATGTGGAAAAATACCTATTCTGGAAAAAAGAAAT
GCCAGCAAACCCCAAGGCCGAATTGTCGGGGGCAGGGTGTGCCCCAAAGGGGAGTGTCCA
TGGCAGGTCCTGTTGTTGGTGAATGGAGCTCAGCTGTGTGGAGGGACCCTGATAAACACC
ATCTGGGTGGTCTCTGCGGCCCACTGTTTCGACAAAATCAAGAGCTGGAGGAACTTGACC
GCGGTGCTGGGCGAGCACGACCTCAGCGAGCACGAAGGGGATGAGCAGAGCCGGCGGGTG
GCGCAGGTCATCATCCCCAGCACGTATGTCCTGGGCGCCACCAACCACGACATCGCGCTG
CTCCGCCTGCAGCAGCCCGTGGTCCTCACTGACCATGTGGTGCCCCTCTGCCTGCCCGAA
CGGACGTTCTCCGAGAGGACGCTGGCCTTCGTGCGCTTCTCGTTGGTCAGCGGCTGGGGT
CAGCTGCTGGACCGTGGTGCCACAGCCCTGGAGCTCATGGCCCTCAACGTGCCCCGGCTG
ATGACCCAGGACTGCCTGCAGCAGTCACAGAAGGCAGAAGCCTCCCCGAATATCACGGAG
TACATGTTCTGTGCCGGCTACTCGGACGGCAGCAGGGACTCCTGCAAGGGGGACAGTGGA
GGCCCACACGCCACCCGCTACCGGGGCACGTGGTACCTGACAGGCATCGTCAGCTGGGGC
CAGGGCTGCGCGGCCGTGGGCCACTTCGGGGTGTACACCAGGGTCTCCCAGTACATCGAG
TGGCTGCAAAAGCTCATGCACTCAGAGCCACGCCCAGGCGTCCTCCTGCGAGCCCCATTT
CCCTAG
```

FIG. 12

SEQUENCE LISTING

<160> NUMBER OF SEQ ID NOS: 155

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ggaucaucuc aagucuuact t                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
guaagacuug agaugaucct t                                            21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
cuuacgcuga guacuucgat t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
ucgaaguacu cagcguaagt t                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 5
gacgcuggcc uucgugcgct t                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
gcgcacgaag gccagcguct t                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
ccucugccug cccgaacggt t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
ccguucgggc aggcagaggt t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ccuucgaggg ccggaacugt t                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 10
caguuccggc ccucgaaggt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ccaaccacga caucgcgcut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
agcgcgaugu cgugguuggt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cucccaguac aucgaguggt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
ccacucgaug uacugggagt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 15
caaccacgac aucgcgcugt t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
cagcgcgaug ucgugguugt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
caguccuaua ucugcuucut t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
agaagcagau auaggacugt t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ccauggcagg uccuguuugt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 20
acaacaggac cugccauggt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
cucugccugc ccgaacggat t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
uccguucggg caggcagagt t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
cggcggcugu gagcaguact t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
guacugcuca cagccgccgt t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 25
uucugugccg gcuacucggt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
ccgaguagcc ggcacagaat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
gaccagcucc aguccuauat t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
uauaggacug gagcugguct t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29 uuguuggguga auggagcuct t                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 30
gagcuccauu caccaacaat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31 auuggaaaa auaccuauut t                                               21
```
(Note: SEQ 31 shown as "auguggaaaa auaccuauut t")
```
<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
aauagguauu uuuccacaut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
gugguccuca cugaccaugt t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
cauggucagu gaggaccact t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

<400> SEQUENCE: 35
acgacaucgc gcugcuccgt t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
cggagcagcg cgaugucgut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
caaggaccag cuccagucct t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
ggacuggagc ugguccuugt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
gcaaggacca gcuccaguct t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 40
gacuggagcu gguccuugct t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
aaggaccagc uccaguccut t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
aggacuggag cugguccuut t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
ccagggucuc ccaguacaut t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
auguacuggg agacccuggt t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 45
cauggcaggu ccuguuguut t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
aacaacagga ccugccaugt t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
acggcggcug ugagcaguat t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
uacugcucac agccgccgut t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
cugugagcag uacugcagut t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 50
acugcaguac ugcucacagt t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
cggugcuggg cgagcacgat t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
ucgugcucgc ccagcaccgt t                                              21

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gacgcuggcc uucgugcgc                                                 19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gcgcacgaag gccagcguc                                                 19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ccucugccug cccgaacgg                                                 19

<210> SEQ ID NO 56
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 56
ccguucgggc aggcagagg                                                      19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccuucgaggg ccggaacug                                                      19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caguuccggc ccucgaagg                                                      19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ccaaccacga caucgcgcu                                                      19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
agcgcgaugu cgugguugg                                                      19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cucccaguac aucgagugg                                                      19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 62
ccacucgaug uacugggag                    19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
caaccacgac aucgcgcug                    19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cagcgcgaug ucgugguug                    19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caguccuaua ucugcuucu                    19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
agaagcagau auaggacug                    19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ccauggcagg uccuguugu                    19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 68
acaacaggac cugccaugg                                              19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cucugccugc ccgaacgga                                              19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uccguucggg caggcagag                                              19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cggcggcugu gagcaguac                                              19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
guacugcuca cagccgccg                                              19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uucugugccg gcuacucgg                                              19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
```

```
ccgaguagcc ggcacagaa                                                  19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gaccagcucc aguccuaua                                                  19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uauaggacug gagcugguc                                                  19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uuguugguga auggagcuc                                                  19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gagcuccauu caccaacaa                                                  19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79 auggaaaa auaccuauu                                                    19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
aauagguauu uuccacau                                                   19
```

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gugguccuca cugaccaug                                               19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cauggucagu gaggaccac                                               19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
acgacaucgc gcugcuccg                                               19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cggagcagcg cgaugucgu                                               19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
caaggaccag cuccagucc                                               19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ggacuggagc ugguccuug                                               19

<210> SEQ ID NO 87

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcaaggacca gcuccaguc                                                19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gacuggagcu gguccuugc                                                19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aaggaccagc uccaguccu                                                19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aggacuggag cugguccuu                                                19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ccagggucuc ccaguacau                                                19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auguacuggg agacccugg                                                19

<210> SEQ ID NO 93
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 93
cauggcaggu ccuguuguu                                                    19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aacaacagga ccugccaug                                                    19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
acggcggcug ugagcagua                                                    19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uacugcucac agccgccgu                                                    19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cugugagcag uacugcagu                                                    19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
acugcaguac ugcucacag                                                    19

<210> SEQ ID NO 99
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 99
cggugcuggg cgagcacga                                                  19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucgugcucgc ccagcaccg                                                  19

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 101
gacgcuggcc uucgugcgcn n                                               21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 102
gcgcacgaag gccagcgucn n                                               21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 103
ccucugccug cccgaacggn n                                               21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide
<220> FEATURE:
<221> NAME/KEY: modified_base
<222> LOCATION: (20)..(21)
<223> OTHER INFORMATION: g, a, c or t

<400> SEQUENCE: 104
ccguucgggc aggcagaggn n                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide
<220> FEATURE:
<221> NAME/KEY: modified_base
<222> LOCATION: (20)..(21)
<223> OTHER INFORMATION: g, a, c or t

<400> SEQUENCE: 105
ccuucgaggg ccggaacugn n                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide
<220> FEATURE:
<221> NAME/KEY: modified_base
<222> LOCATION: (20)..(21)
<223> OTHER INFORMATION: g, a, c or t

<400> SEQUENCE: 106
caguuccggc ccucgaaggn n                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide
<220> FEATURE:
<221> NAME/KEY: modified_base
<222> LOCATION: (20)..(21)
<223> OTHER INFORMATION: g, a, c or t

<400> SEQUENCE: 107
ccaaccacga caucgcgcun n                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 108
agcgcgaugu cgugguuggn n                                                 21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 109
cucccaguac aucgaguggn n                                                 21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 110
ccacucgaug uacugggagn n                                                 21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 111
caaccacgac aucgcgcugn n                                                 21

```
<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 112
cagcgcgaug ucgugguugn n                                                   21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 113
caguccuaua ucugcuucun n                                                   21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 114
agaagcagau auaggacugn n                                                   21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 115
ccauggcagg uccuguugn n                                                    21
```

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 116
acaacaggac cugccauggn n                                                 21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 117
cucugccugc ccgaacggan n                                                 21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 118
uccguucggg caggcagagn n                                                 21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 119
cggcggcugu gagcaguacn n                                                 21

```
<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 120
guacugcuca cagccgccgn n                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 121
uucugugccg gcuacucggn n                                             21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 122
ccgaguagcc ggcacagaan n                                             21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 123
gaccagcucc aguccuauan n                                             21
```

```
<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 124
uauaggacug gagcuggucn n                                                    21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 125
uuguugguga auggagcucn n                                                    21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 126
gagcuccauu caccaacaan n                                                    21

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 127 auggaaaa auaccuauun n                                                      21
```

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 128
aauagguauu uuuccacaun n                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 129
gugguccuca cugaccaugn n                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 130
cauggucagu gaggaccacn n                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 131
acgacaucgc gcugcuccgn n                                              21

```
<210> SEQ ID NO 132
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 132
cggagcagcg cgaugucgun n                                                   21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 133
caaggaccag cuccaguccn n                                                   21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 134
ggacuggagc ugguccuugn n                                                   21

<210> SEQ ID NO 135
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 135
gcaaggacca gcuccagucn n                                                   21
```

```
<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 136
gacuggagcu gguccuugcn n                                                 21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 137
aaggaccagc uccaguccun n                                                 21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 138
aggacuggag cugguccuun n                                                 21

<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 139
ccagggucuc ccaguacaun n                                                 21
```

```
<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 140
auguacuggg agacccuggn n                                                   21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 141
cauggcaggu ccuguuguun n                                                   21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 142
aacaacagga ccugccaugn n                                                   21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 143
acggcggcug ugagcaguan n                                                   21
```

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 144
uacugcucac agccgccgun n                                             21

<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 145
cugugagcag uacugcagun n                                             21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 146
acugcaguac ugcucacagn n                                             21

<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: g, a, c or t

<400> SEQUENCE: 147
cggugcuggg cgagcacgan n                                             21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: g, a, c or t

<400> SEQUENCE: 148
ucgugcucgc ccagcaccgn n                                              21

<210> SEQ ID NO 149
<211> LENGTH: 3141
<212> TYPE: DNA
<213> ORGANISM: Homo sapiens

<400> SEQUENCE: 149
agtcccatgg ggaatgtcaa caggcagggg cagcactgca gagatttcat catggtctcc     60
caggccctca ggctcctctg ccttctgctt gggcttcagg gctgcctggc tgcaggcggg    120
gtcgctaagg cctcaggagg agaaacacgg gacatgccgt ggaagccggg gcctcacaga    180
gtcttcgtaa cccaggagga agcccacggc gtcctgcacc ggcgccggcg cgccaacgcg    240
ttcctggagg agctgcggcc gggctccctg gagagggagt gcaaggagga gcagtgctcc    300
ttcgaggagg cccgggagat cttcaaggac gcggagagga cgaagctgtt ctggatttct    360
tacagtgatg gggaccagtg tgcctcaagt ccatgccaga atgggggctc ctgcaaggac    420
cagctccagt cctatatctg cttctgcctc cctgccttcg agggccggaa ctgtgagacg    480
cacaaggatg accagctgat ctgtgtgaac gagaacggcg gctgtgagca gtactgcagt    540
gaccacacgg gcaccaagcg ctcctgtcgg tgccacgagg ggtactctct gctggcagac    600
ggggtgtcct gcacacccac agttgaatat ccatgtggaa aaataccat tctagaaaaa    660 agaaatgcca gcaaacccca aggccgaatt gtggggggca aggtgtgccc caaaggggag    720
tgtccatggc aggtcctgtt gttggtgaat ggagctcagt tgtgtggggg accctgatc    780 aacaccatct gggtggtctc cgcggcccac tgtttcgaca aaatcaagaa ctggaggaac    840
ctgatcgcgc tgctgggcga gcacgacctc agcgagcacg acgggatgga gcagagccgg    900
cgggtggcgc aggtcatcat ccccagcacg tacgtcccgg gcaccaccaa ccacgacatc    960
gcgctgctcc gcctgcacca gcccgtggtc tcactgacca tgtggtgcc cctctgcctg   1020 cccgaacgga cgttctctga ggacgctg gccttcgtgc gcttctcatt ggtcagcggc   1080
tggggccagc tgctggaccg tggcgccacg gccctggagc tcatggtcct caacgtgccc   1140
cggctgatga cccaggactg cctgcagcag tcacggaagg tgggagactc cccaaatatc   1200
acggagtaca tgttctgtgc cggctactcg gatggcagca aggactcctg caaggggac   1260 agtggaggcc cacatgccac ccactaccgg ggcacgtggt acctgacggg catcgtcagc   1320
tggggccagg gctgcgcaac cgtgggccac tttgggtgt acaccagggt ctcccagtac    1380
atcgagtggc tgcaaaagct catgcgctca gagccacgcc aggagtcct cctgcgagcc    1440 ccatttccct agcccagcag ccctggcctg tggagagaaa gccaaggctg cgtcgaactg    1500
tcctggcacc aaatcccata tattcttctg cagttaatgg ggtagaggag ggcatgggag    1560

| | | |
|---|---|---|
| ggagggagag gtggggaggg agacagagac agaaacagag agagacagag acagagagag | 1620 | |
| actgagggag agactctgag gacatggaga gagactcaaa gagactccaa gattcaaaga | 1680 | |
| gactaataga gacacagaga tggaatagaa aagatgagag gcagaggcag acaggcgctg | 1740 | |
| gacagagggg caggggagtg ccaaggttgt cctggaggca gacagcccag ctgagcctcc | 1800 | |
| ttacctccct tcagccaagc ccacctgcac gtgatctgct ggcctcaggc tgctgctctg | 1860 | |
| ccttcattgc tggagacagt agaggcatga acacacatgg atgcacacac acacgccaa | 1920 | |
| atgcacacac acagagatat gcacacacac ggatgcacac acagatggtc acacagagat | 1980 | |
| acgcaaacac accgatgcac acgcacatag agatatgcac acacagatgc acacacagat | 2040 | |
| atacacatgg atgcacgcac atgccaatgc acgcacacat cagtgcacac ggatgcacag | 2100 | |
| agatatgcac acaccgatgt gcgcacacac agatatgcac acatggat gagcacacac | 2160 | |
| acaccaatgc gcacacacac cgatgtacac acacagatgc acacagat gcacacacac | 2220 | |
| cgatgctgac tccatgtgtg ctgtcctctg aaggcggttg tttagctctc acttttctgg | 2280 | |
| ttcttatcca ttatcatctt cacttcagac aattcagaag catcaccatg catggtggcg | 2340 | |
| aatgcccca aactctcccc caaatgtatt tctcccttcg ctgggtgccg ggctgcacag | 2400 | |
| actattcccc acctgcttcc cagcttcaca ataaacggct gcgtctcctc cgcacacctg | 2460 | |
| tggtgcctgc cacccactgg gttgcccatg attcattttt ggagccccg gtgctcatcc | 2520 | |
| tctgagatgc tcttttcttt cacaattttc aacatcactg aaatgaaccc tcacatggaa | 2580 | |
| gctattttt aaaacaaaa gctgtttgat agatgtttga ggctgtagct cccaggatcc | 2640 | |
| tgtggaattg gatgttctct ccctgccaca gcccttgtca atgatatttc acagagaccc | 2700 | |
| tgggagcacc tgctcaagag tcagggacac acgcatcact aaatgcaagt tcccaggccc | 2760 | |
| tggctgcagt gggaggacct ggcaagctgc actcttgctg agtccccagg gtggtggaag | 2820 | |
| aagaatgaga aacacatgaa cagagaaatg gggaggtgac aaacagtgcc cccactcaga | 2880 | |
| ctccggcaag cacggctcag agagtggact cgatgccatc cctgcagggc cgtcctgggc | 2940 | |
| accactggca ctcacagcag caaggtgggc accattggca ctcacagcag caaggcaggc | 3000 | |
| accagcaacc cacctcgggg gcactcaggc atcatctact tcagagcaga cagggtctat | 3060 | |
| gaactacagc cgtgggctgc ttccaaggca ccctgctctt gtaaataaag ttttatggga | 3120 | |
| acacaaaaaa aaaaaaaaaa a | 3141 | |

<210> SEQ ID NO 150
<211> LENGTH: 3075
<212> TYPE: DNA
<213> ORGANISM: Homo sapiens

<400> SEQUENCE: 150

| | | |
|---|---|---|
| agtcccatgg ggaatgtcaa caggcagggg cagcactgca gagatttcat catggtctcc | 60 | |
| caggccctca ggctcctctg ccttctgctt gggcttcagg gctgcctggc tgcagtcttc | 120 | |
| gtaacccagg aggaagccca cggcgtcctg caccggcgcc ggcgcgccaa cgcgttcctg | 180 | |
| gaggagctgc ggccgggctc cctggagagg gagtgcaagg aggagcagtg ctccttcgag | 240 | |
| gaggcccggg agatcttcaa ggacgcggag aggacgaagc tgttctggat tcttacagt | 300 | |
| gatgggacc agtgtgcctc aagtccatgc cagaatgggg gctcctgcaa ggaccagctc | 360 | |
| cagtcctata tctgcttctg cctccctgcc ttcgagggcc ggaactgtga gacgcacaag | 420 | |
| gatgaccagc tgatctgtgt gaacgagaac ggcggctgtg agcagtactg cagtgaccac | 480 | |
| acgggcacca agcgctcctg tcggtgccac gagggggtact ctctgctggc agacggggtg | 540 | |

| | |
|---|---|
| tcctgcacac ccacagttga atatccatgt ggaaaaatac ctattctaga aaaaagaaat | 600 |
| gccagcaaac cccaaggccg aattgtgggg ggcaaggtgt gccccaaagg ggagtgtcca | 660 |
| tggcaggtcc tgttgttggt gaatggagct cagttgtgtg gggggaccct gatcaacacc | 720 |
| atctgggtgg tctccgcggc ccactgtttc gacaaaatca agaactggag gaacctgatc | 780 |
| gcggtgctgg gcgagcacga cctcagcgag cacgacgggg atgagcagag ccggcgggtg | 840 |
| gcgcaggtca tcatccccag cacgtacgtc ccgggcacca caaccacga catcgcgctg | 900 |
| ctccgcctgc accagcccgt ggtcctcact gaccatgtgg tgcccctctg cctgcccgaa | 960 |
| cggacgttct ctgagaggac gctggccttc gtgcgcttct cattggtcag cggctggggc | 1020 |
| cagctgctgg accgtggcgc cacggccctg gagctcatgg tcctcaacgt gccccggctg | 1080 |
| atgacccagg actgcctgca gcagtcacgg aaggtgggag actccccaaa tatcacggag | 1140 |
| tacatgttct gtgccggcta ctcggatggc agcaaggact cctgcaaggg ggacagtgga | 1200 |
| ggcccacatg ccacccacta ccggggcacg tggtacctga cgggcatcgt cagctggggc | 1260 |
| cagggctgcg caaccgtggg ccactttggg gtgtacacca gggtctccca gtacatcgag | 1320 |
| tggctgcaaa agctcatgcg ctcagagcca cgcccaggag tcctcctgcg agccccattt | 1380 |
| ccctagccca gcagccctgg cctgtggaga aaagccaag gctgcgtcga actgtcctgg | 1440 |
| caccaaatcc catatattct tctgcagtta atggggtaga ggagggcatg ggagggaggg | 1500 |
| agaggtgggg agggagacag agacagaaac agagagagac agagacagag agagactgag | 1560 |
| ggagagactc tgaggacatg gagagagact caaagagact ccaagattca aagagactaa | 1620 |
| tagagacaca gagatggaat agaaaagatg agaggcagag gcagacaggc gctggacaga | 1680 |
| ggggcagggg agtgccaagg ttgtcctgga ggcagacagc ccagctgagc ctccttacct | 1740 |
| cccttcagcc aagcccacct gcacgtgatc tgctggcctc aggctgctgc tctgccttca | 1800 |
| ttgctggaga cagtagaggc atgaacacac atggatgcac acacacacac gccaatgcac | 1860 |
| acacacagag atatgcacac acacggatgc acacacagat ggtcacacag agatacgcaa | 1920 |
| acacaccgat gcacacgcac atagagatat gcacacacag atgcacacac agatatacac | 1980 |
| atggatgcac gcacatgcca atgcacgcac acatcagtgc acacggatgc acagagatat | 2040 |
| gcacacaccg atgtgcgcac acacagatat gcacacacat ggatgagcac acacacacca | 2100 |
| atgcgcacac acaccgatgt acacacacag atgcacacac agatgcacac acaccgatgc | 2160 |
| tgactccatg tgtgctgtcc tctgaaggcg gttgtttagc tctcactttt ctggttctta | 2220 |
| tccattatca tcttcacttc agacaattca gaagcatcac catgcatggt ggcgaatgcc | 2280 |
| cccaaactct cccccaaatg tatttctccc ttcgctgggt gccgggctgc acagactatt | 2340 |
| ccccacctgc ttcccagctt cacaataaac ggctgcgtct cctccgcaca cctgtggtgc | 2400 |
| ctgccaccca ctgggttgcc catgattcat ttttggagcc cccggtgctc atcctctgag | 2460 |
| atgctctttt ctttcacaat tttcaacatc actgaaatga accctcacat ggaagctatt | 2520 |
| ttttaaaaac aaaagctgtt tgatagatgt ttgaggctgt agctcccagg atcctgtgga | 2580 |
| attggatgtt ctctccctgc cacagcccctt gtcaatgata tttcacagag accctgggag | 2640 |
| cacctgctca agagtcaggg acacacgcat cactaaatgc aagttcccag gccctggctg | 2700 |
| cagtgggagg acctggcaag ctgcactctt gctgagtccc cagggtggtg gaagaagaat | 2760 |
| gagaaacaca tgaacagaga aatggggagg tgacaaacag tgcccccact cagactccgg | 2820 |
| caagcacggc tcagagagtg gactcgatgc catccctgca gggccgtcct gggcaccact | 2880 |
| ggcactcaca gcagcaaggt gggcaccatt ggcactcaca gcagcaaggc aggcaccagc | 2940 |

| | | | | |
|---|---|---|---|---|
| aacccacctc | gggggcactc | aggcatcatc | tacttcagag | cagacagggt ctatgaacta | 3000 |
| cagccgtggg | ctgcttccaa | ggcaccctgc | tcttgtaaat | aaagttttat gggaacacaa | 3060 |
| aaaaaaaaaa | aaaaa | | | | 3075 |

<210> SEQ ID NO 151
<211> LENGTH: 2424
<212> TYPE: DNA
<213> ORGANISM: Macaca mulatta

<400> SEQUENCE: 151

| | | | | | |
|---|---|---|---|---|---|
| ggccattacg | gccggggatt | tcatcatggt | ctctcgagcc | ctcgggctcc tctgccttct | 60 |
| gcttgggctt | cagggctgtc | tggctgcagc | caccttcctg | ccccaggcgg ggtcgctgag | 120 |
| gcctcaggag | gagaaaacac | aggacctgct | gtggaagcca | gggcctcaca gagtcttcgt | 180 |
| aacccaggag | gaagcccatg | gcgtcctgca | caggcagcgg | cgcgccaact cgttcctgga | 240 |
| ggagctgcgg | ccgggctccc | tggagaggga | gtgcaaggag | gagcaatgct ccttcgagga | 300 |
| ggcccgggag | atcttcaagg | acctggagag | gacgaagctg | ttctggattt cttacagtga | 360 |
| tggggaccag | tgtgcctcaa | atccgtgcca | gaatgggggc | tcctgcaagg accagctcca | 420 |
| gtcctatatc | tgcttctgcc | tcccttcctt | cgagggccgg | aactgtgaga gaacaagga | 480 |
| tgaccagctg | atctgcgtga | cgagaacgg | cggctgtgag | cagtactgca gtgaccacgc | 540 |
| gggtgccaag | cgctcctgtt | ggtgccacga | ggggtactcg | ctgctggcag acggggtgtc | 600 |
| ctgcatgccc | acagttgaat | atccatgtgg | aaaaatacct | attctggaaa aagaaatgc | 660 |
| cagcaaaccc | caaggccgaa | ttgtcggggg | cagggtgtgc | cccaaggggg agtgtccatg | 720 |
| gcaggtcctg | ttgttggtga | atggagctca | gctgtgtgga | gggaccctga taaacaccat | 780 |
| ctgggtggtc | tctgcggccc | actgttttga | caaaatcaag | agctggagga acttgaccgc | 840 |
| ggtgctgggc | gagcacgacc | tcagcgagca | cgaaggggat | gagcagagcc ggcgggtggc | 900 |
| gcaggtcatc | atccccagca | cgtatgtcct | gggcgccacc | aaccacgaca tcgcgctgct | 960 |
| ccgcctgcag | cagcccgtgg | tcctcactga | ccatgtggtg | cccctctgcc tgcccgaacg | 1020 |
| gatgttctcc | gagaggacgc | tggccttcgt | gcgcttctcg | ttggtcagcg gctggggtca | 1080 |
| gctgctggac | cgtggtgcca | cagccctgga | gctcatggcc | ctcaacgtgc ccggctgat | 1140 |
| gacccaggac | tgcctgcagc | agtcacagaa | ggcagaagcc | tccccgaata tcacggagta | 1200 |
| catgttctgt | gccggctact | cggacggcag | cagggactcc | tgcaagggg acagtggagg | 1260 |
| cccacacgcc | acccgctacc | ggggcacgtg | gtacctgaca | ggcatcgtca gctggggcca | 1320 |
| gggctgcgca | gccgtgggcc | acttcggggt | gtacaccagg | gtctcccagt catcgagtg | 1380 |
| gctgcaaaag | ctcatgcact | cagagccacg | cccaggcgtc | ctcctgcgag ccccatttcc | 1440 |
| ctagcctagc | agccctgccc | cctggagaga | aagccaaggc | tgtgtagaac tgttctggca | 1500 |
| caaaatccca | tcgattcttc | tgcagttcat | ggggtagagg | agggcatggg agggagggag | 1560 |
| aggtggggag | ggagacagag | acagaaacag | agagacaaag | agacagggag agactgaggg | 1620 |
| agaggttctg | aggacatgga | gagactcaaa | gagactccaa | gattcaaaga gcctaataga | 1680 |
| gacacagaga | aggaatcgaa | aagatgagat | gcagaggcag | acaggcgctg gacagagggg | 1740 |
| caggggaatg | ccgcggttgt | cctggaggca | gacagcccag | ctgagcctcc ttatctctct | 1800 |
| tcagccaagc | ccacctgccc | gtgatctgct | ggcctcaggc | tgctgttctg ccttcattgc | 1860 |
| tggagacact | agaggcatgt | acacatgtgg | atgcatacac | acacaccaat gcacacacag | 1920 |
| agatatgcac | acacagaggg | tcacacagag | atatgcaaac | acactgatac acacacatac | 1980 |

-continued

| | |
|---|---|
| agagatatgc acatacacgg atgcatatac acagatatgc ccacacacag atgcgtgcac | 2040 |
| accacaccaa tgcacgcaca cactaatgca cccacacgga tgcagagaga tatgcacaca | 2100 |
| ccgatgtgca catacacaga tatgcacaca catggatgag tgcacacaca ctaatgtaca | 2160 |
| cacacagata tgcacacacg gatgcacaca caccgatgct gactccatgt gtgctgtcct | 2220 |
| ccaaaggcgg ttgtttagct ctcactttc tcgttcttat ccattatcat cttcatttca | 2280 |
| gacaattcag aagcatcacc atgcatgttg gcaaatgccc caaactctcc cccaaatgtg | 2340 |
| ccgggctgca caggccgttc cccaccggct tcccaacttc acaataaatg gctgcatctc | 2400 |
| ctccgcaaaa aaaaaaaaaa aaaa | 2424 |

<210> SEQ ID NO 152
<211> LENGTH: 478
<212> TYPE: DNA
<213> ORGANISM: Macaca mulatta

<400> SEQUENCE: 152

| | |
|---|---|
| cgagcacgaa ggggatgagc agagccggcg ggtggcgcag gtcatcatcc ccagcacgta | 60 |
| tgtcctgggc gccaccaacc acgacatcgc gctgctccgc ctgcagcagc ccgtggtcct | 120 |
| cactgaccat gtggtgcccc tctgcctgcc cgaacggatg ttctccgaga ggacgctggc | 180 |
| cttcgtgcgc ttctcattgg tcagcggctg gggtcagctg ctggaccgtg gtgccacagc | 240 |
| cctggagctc atggccctca acgtgccccg gctgatgacc caggactgcc tgcagcagtc | 300 |
| acagaaggca gaagcctccc cgaatatcac ggagtacatg ttctgtgccg gctactcgga | 360 |
| cggcagcagg gactcctgca aggggacag tgaggcccca cacgccaccc gctaccgggg | 420 |
| cacgtggtac ctgacaggca tcgtcagctg gggccagggc tgcgcagccg tgggccac | 478 |

<210> SEQ ID NO 153
<211> LENGTH: 1389
<212> TYPE: DNA
<213> ORGANISM: Macaca mulatta
<220> FEATURE:
<221> NAME/KEY: CDS
<222> LOCATION: (1)..(1386)

<400> SEQUENCE: 153

| | |
|---|---|
| atg gtc tct cga gcc ctc ggg ctc ctc tgc ctt ctg ctt ggg ctt cag<br>Met Val Ser Arg Ala Leu Gly Leu Leu Cys Leu Leu Leu Gly Leu Gln<br>1               5                   10                  15 | 48 |
| ggc tgt ctg gct gca ggc ggg gtc gct gag gcc tca gga gga gaa cag<br>Gly Cys Leu Ala Ala Gly Gly Val Ala Glu Ala Ser Gly Gly Glu Gln<br>            20                  25                  30 | 96 |
| gac ctg ctg tgg aag cca ggg cct cac aga gga cgc ctc aca caa gac<br>Asp Leu Leu Trp Lys Pro Gly Pro His Arg Gly Arg Leu Thr Gln Asp<br>        35                  40                  45 | 144 |
| acc tca cat ggt gca ctt cac act cac agg tca cct cac att cga cac<br>Thr Ser His Gly Ala Leu His Thr His Arg Ser Pro His Ile Arg His<br>    50                  55                  60 | 192 |
| ctc aca ctg agc aca ctt cac act cgg gac acc tca cac tca ggt tcc<br>Leu Thr Leu Ser Thr Leu His Thr Arg Asp Thr Ser His Ser Gly Ser<br>65                  70                  75                  80 | 240 |
| cca acc cca gct cgt ggt ttg tcc agt gct cac cgt tgg aag ctg ttc<br>Pro Thr Pro Ala Arg Gly Leu Ser Ser Ala His Arg Trp Lys Leu Phe<br>                85                  90                  95 | 288 |
| tgg att tct tac agt gat ggg gac cag tgt gcc tca aat ccg tgc cag<br>Trp Ile Ser Tyr Ser Asp Gly Asp Gln Cys Ala Ser Asn Pro Cys Gln<br>            100                 105                 110 | 336 |
| aat ggg ggc tcc tgc aag gac cag ctc cag tcc tat atc tgc ttc tgc<br> | 384 |

```
                Asn Gly Gly Ser Cys Lys Asp Gln Leu Gln Ser Tyr Ile Cys Phe Cys
                    115                 120                 125 ctc cct tcc ttc gag ggc cgg aac tgt gag aag aac aag gat gac cag        432
Leu Pro Ser Phe Glu Gly Arg Asn Cys Glu Lys Asn Lys Asp Asp Gln
130                 135                 140 ctg atc tgc gtg aac gag aac ggc tgt gag cag tac tgc agt gac            480
Leu Ile Cys Val Asn Glu Asn Gly Cys Glu Gln Tyr Cys Ser Asp
145                 150                 155                 160 cac gcg ggt gcc aag cgc tcc tgt tgg tgc cac gag ggg tac tcg ctg        528
His Ala Gly Ala Lys Arg Ser Cys Trp Cys His Glu Gly Tyr Ser Leu
                165                 170                 175 ctg gca gac ggg gtg tcc tgc atg ccc aca gtt gaa tat cca tgt gga        576
Leu Ala Asp Gly Val Ser Cys Met Pro Thr Val Glu Tyr Pro Cys Gly
            180                 185                 190 aaa ata cct att ctg gaa aaa aga aat gcc agc aaa ccc caa ggc cga        624
Lys Ile Pro Ile Leu Glu Lys Arg Asn Ala Ser Lys Pro Gln Gly Arg
        195                 200                 205 att gtc ggg ggc agg gtg tgc ccc aaa ggg gag tgt cca tgg cag gtc        672
Ile Val Gly Gly Arg Val Cys Pro Lys Gly Glu Cys Pro Trp Gln Val
    210                 215                 220 ctg ttg ttg gtg aat gga gct cag ctg tgt gga ggg acc ctg ata aac        720
Leu Leu Leu Val Asn Gly Ala Gln Leu Cys Gly Gly Thr Leu Ile Asn
225                 230                 235                 240 acc atc tgg gtg gtc tct gcg gcc cac tgt ttc gac aaa atc aag agc        768
Thr Ile Trp Val Val Ser Ala Ala His Cys Phe Asp Lys Ile Lys Ser
                245                 250                 255 tgg agg aac ttg acc gcg gtg ctg ggc gag cac gac ctc agc gag cac        816
Trp Arg Asn Leu Thr Ala Val Leu Gly Glu His Asp Leu Ser Glu His
            260                 265                 270 gaa ggg gat gag cag agc cgg cgg gtg gcg cag gtc atc atc ccc agc        864
Glu Gly Asp Glu Gln Ser Arg Arg Val Ala Gln Val Ile Ile Pro Ser
        275                 280                 285 acg tat gtc ctg ggc gcc acc aac cac gac atc gcg ctg ctc cgc ctg        912
Thr Tyr Val Leu Gly Ala Thr Asn His Asp Ile Ala Leu Leu Arg Leu
    290                 295                 300 cag cag ccc gtg gtc ctc act gac cat gtg gtg ccc ctc tgc ctg ccc        960
Gln Gln Pro Val Val Leu Thr Asp His Val Val Pro Leu Cys Leu Pro
305                 310                 315                 320 gaa cgg acg ttc tcc gag agg acg ctg gcc ttc gtg cgc ttc tcg ttg       1008
Glu Arg Thr Phe Ser Glu Arg Thr Leu Ala Phe Val Arg Phe Ser Leu
                325                 330                 335 gtc agc ggc tgg ggt cag ctg ctg gac cgt ggt gcc aca gcc ctg gag       1056
Val Ser Gly Trp Gly Gln Leu Leu Asp Arg Gly Ala Thr Ala Leu Glu
            340                 345                 350 ctc atg gcc ctc aac gtg ccc cgg ctg atg acc cag gac tgc ctg cag       1104
Leu Met Ala Leu Asn Val Pro Arg Leu Met Thr Gln Asp Cys Leu Gln
        355                 360                 365 cag tca cag aag gca gaa gcc tcc ccg aat atc acg gag tac atg ttc       1152
Gln Ser Gln Lys Ala Glu Ala Ser Pro Asn Ile Thr Glu Tyr Met Phe
    370                 375                 380 tgt gcc ggc tac tcg gac ggc agc agg gac tcc tgc aag ggg gac agt       1200
Cys Ala Gly Tyr Ser Asp Gly Ser Arg Asp Ser Cys Lys Gly Asp Ser
385                 390                 395                 400 gga ggc cca cac gcc acc cgc tac cgg ggc acg tgg tac ctg aca ggc       1248
Gly Gly Pro His Ala Thr Arg Tyr Arg Gly Thr Trp Tyr Leu Thr Gly
                405                 410                 415 atc gtc agc tgg ggc cag ggc tgc gcg gcc gtg ggc cac ttc ggg gtg       1296
Ile Val Ser Trp Gly Gln Gly Cys Ala Ala Val Gly His Phe Gly Val
            420                 425                 430 tac acc agg gtc tcc cag tac atc gag tgg ctg caa aag ctc atg cac       1344
Tyr Thr Arg Val Ser Gln Tyr Ile Glu Trp Leu Gln Lys Leu Met His
```

```
Tyr Thr Arg Val Ser Gln Tyr Ile Glu Trp Leu Gln Lys Leu Met His
        435                 440                 445 tca gag cca cgc cca ggc gtc ctc ctg cga gcc cca ttt ccc tag         1389
Ser Glu Pro Arg Pro Gly Val Leu Leu Arg Ala Pro Phe Pro
    450                 455                 460
```

<210> SEQ ID NO 154
<211> LENGTH: 462
<212> TYPE: PRT
<213> ORGANISM: Macaca mulatta

<400> SEQUENCE: 154

```
Met Val Ser Arg Ala Leu Gly Leu Leu Cys Leu Leu Leu Gly Leu Gln
1               5                   10                  15

Gly Cys Leu Ala Ala Gly Gly Val Ala Glu Ala Ser Gly Gly Glu Gln
            20                  25                  30

Asp Leu Leu Trp Lys Pro Gly Pro His Arg Gly Arg Leu Thr Gln Asp
        35                  40                  45

Thr Ser His Gly Ala Leu His Thr Arg Ser Pro His Ile Arg His
50                  55                  60

Leu Thr Leu Ser Thr Leu His Thr Arg Asp Thr Ser His Ser Gly Ser
65                  70                  75                  80

Pro Thr Pro Ala Arg Gly Leu Ser Ser Ala His Arg Trp Lys Leu Phe
                85                  90                  95

Trp Ile Ser Tyr Ser Asp Gly Asp Gln Cys Ala Ser Asn Pro Cys Gln
            100                 105                 110

Asn Gly Gly Ser Cys Lys Asp Gln Leu Gln Ser Tyr Ile Cys Phe Cys
        115                 120                 125

Leu Pro Ser Phe Glu Gly Arg Asn Cys Glu Lys Asn Lys Asp Asp Gln
130                 135                 140

Leu Ile Cys Val Asn Glu Asn Gly Gly Cys Glu Gln Tyr Cys Ser Asp
145                 150                 155                 160

His Ala Gly Ala Lys Arg Ser Cys Trp Cys His Glu Gly Tyr Ser Leu
                165                 170                 175

Leu Ala Asp Gly Val Ser Cys Met Pro Thr Val Glu Tyr Pro Cys Gly
            180                 185                 190

Lys Ile Pro Ile Leu Glu Lys Arg Asn Ala Ser Lys Pro Gln Gly Arg
        195                 200                 205

Ile Val Gly Gly Arg Val Cys Pro Lys Gly Glu Cys Pro Trp Gln Val
210                 215                 220

Leu Leu Leu Val Asn Gly Ala Gln Leu Cys Gly Gly Thr Leu Ile Asn
225                 230                 235                 240

Thr Ile Trp Val Val Ser Ala Ala His Cys Phe Asp Lys Ile Lys Ser
                245                 250                 255

Trp Arg Asn Leu Thr Ala Val Leu Gly Glu His Asp Leu Ser Glu His
            260                 265                 270

Glu Gly Asp Glu Gln Ser Arg Arg Val Ala Gln Val Ile Ile Pro Ser
        275                 280                 285

Thr Tyr Val Leu Gly Ala Thr Asn His Asp Ile Ala Leu Leu Arg Leu
290                 295                 300

Gln Gln Pro Val Val Leu Thr Asp His Val Val Pro Leu Cys Leu Pro
305                 310                 315                 320

Glu Arg Thr Phe Ser Glu Arg Thr Leu Ala Phe Val Arg Phe Ser Leu
                325                 330                 335

Val Ser Gly Trp Gly Gln Leu Leu Asp Arg Gly Ala Thr Ala Leu Glu
            340                 345                 350
```

```
Leu Met Ala Leu Asn Val Pro Arg Leu Met Thr Gln Asp Cys Leu Gln
            355                 360                 365

Gln Ser Gln Lys Ala Glu Ala Ser Pro Asn Ile Thr Glu Tyr Met Phe
        370                 375                 380

Cys Ala Gly Tyr Ser Asp Gly Ser Arg Asp Ser Cys Lys Gly Asp Ser
385                 390                 395                 400

Gly Gly Pro His Ala Thr Arg Tyr Arg Gly Thr Trp Tyr Leu Thr Gly
                405                 410                 415

Ile Val Ser Trp Gly Gln Gly Cys Ala Ala Val Gly His Phe Gly Val
            420                 425                 430

Tyr Thr Arg Val Ser Gln Tyr Ile Glu Trp Leu Gln Lys Leu Met His
        435                 440                 445

Ser Glu Pro Arg Pro Gly Val Leu Leu Arg Ala Pro Phe Pro
    450                 455                 460
```

<210> SEQ ID NO 155
<211> LENGTH: 1326
<212> TYPE: DNA
<213> ORGANISM: Macaca mulatta

<400> SEQUENCE: 155

```
atggtctctc gagccctcgg gctcctctgc cttctgcttg ggcttcaggg ctgtctggct    60
gcaggacgcc tcacacaaga cacctcacat ggtgcacttc acactcacag gtcacctcac   120
attcgacacc tcacactgag cacacttcac actcgggaca cctcacactc aggttcccca   180
accccagctc gtggtttgtc cagtgctcac cgttggaagc tgttctggat ttcttacagt   240
gatggggacc agtgtgcctc aaatccgtgc agaatggggg ctcctgcaa ggaccagctc    300
cagtcctata tctgcttctg cctcccttcc ttcgagggcc ggaactgtga agaacaag    360
gatgaccagc tgatctgcgt gaacgagaac ggcggctgtg agcagtactg cagtgaccac   420
gcgggtgcca agcgctcctg ttggtgccac gaggggtact cgctgctggc agacggggtg   480
tcctgcatgc ccacagttga atatccatgt ggaaaaatac ctattctgga aaaagaaat   540
gccagcaaac cccaaggccg aattgtcggg gcagggtgt gccccaaagg ggagtgtcca    600
tggcaggtcc tgttgttggt gaatggagct cagctgtgtg agggaccct gataaacacc   660
atctgggtgg tctctgcggc ccactgtttc gacaaaatca gagctggag gaacttgacc   720
gcggtgctgg gcgagcacga cctcagcgag cacgaagggg atgagcagag ccggcgggtg   780
gcgcaggtca tcatccccag cacgtatgtc ctgggcgcca ccaaccacga catcgcgctg   840
ctccgcctgc agcagcccgt ggtcctcact gaccatgtgg tgcccctctg cctgcccgaa   900
cggacgttct ccgagaggac gctggccttc gtgcgcttct cgttggtcag cggctggggt   960
cagctgctgg accgtggtgc cacagccctg agctcatgg ccctcaacgt gccccggctg   1020
atgacccagg actgcctgca gcagtcacag aaggcagaag cctccccgaa tatcacggag   1080
tacatgttct gtgccggcta ctcggacggc agcagggact cctgcaaggg ggacagtgga   1140
ggcccacacg ccaccgcta ccggggcacg tggtacctga caggcatcgt cagctgggc    1200
cagggctgcg cggccgtggg ccacttcggg gtgtacacca gggtctccca gtacatcgag   1260
tggctgcaaa agctcatgca ctcagagcca cgcccaggcg tcctcctgcg agccccattt   1320
ccctag                                                              1326
```

COMPOSITIONS AND METHODS FOR INHIBITING EXPRESSION OF FACTOR VII GENE

RELATED APPLICATIONS

This application is a continuation of U.S. application Ser. No. 12/331,708, now U.S. Pat. No. 7,871,985, filed on Dec. 10, 2008, which claims benefit of U.S. Provisional Application No. 61/012,670, filed Dec. 10, 2007, and U.S. Provisional Application No. 61/014,879, filed Dec. 19, 2007, which are incorporated herein in their entirety by reference.

STATEMENT REGARDING FEDERALLY SPONSORED RESEARCH OF DEVELOPMENT

This invention was made with government support under Grant Nos. HHSN26620060012C awarded by the National Institutes of Health. The government has certain rights in the invention.

FIELD OF THE INVENTION

This invention relates to double-stranded ribonucleic acid (dsRNA), and its use in mediating RNA interference to inhibit the expression of the Factor VII gene and the use of the dsRNA to treat or prevent a Factor VII-mediated disorder, e.g., Viral Hemorrhagic Fever.

BACKGROUND OF THE INVENTION

Factor VII (FVII) is involved in coagulation. Upon blood vessel injury, tissue factor (TF), located on the outside of vessels, is exposed to the blood and circulating factor VII. Once bound to TF, FVII is activated to FVIIa by various proteases, including thrombin (factor IIa), activated factor X and the FVIIa-TF complex itself. In addition to its role in initiating coagulation, the TF/FVIIa complex has been reported to have direct proinflammatory effects independent of the activation of coagulation.

A number of viruses have been reported to cause lethal hemorrhagic disease in humans and certain other primates. These viruses are from a number of viral families including Filoviridae, Arenaviridae, Bunyaviridae, and Flaviridae. Patients affected with hemorrhagic fevers typically develop a severe consumptive disseminated intravascular coagulation (DIC). DIC is characterized by wide-spread systematic activation of the coagulation cascade resulting in excess thrombin generation. In addition, activation of the fibrinolytic system coupled with the consumption of coagulation factors results in a depletion of clotting factors and degradation of platelet membrane glycoproteins.

Certain infectious agents are also known to activate the coagulation system following infection. A variety of inflammatory stimuli, including bacterial cell products, viral infection and cytokines have been reported to induce the expression of TF on the surface of endothelial cells and monocytes, thereby activating the coagulation pathway.

Double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of the unc-22 gene in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.).

SUMMARY OF THE INVENTION

The invention provides double-stranded ribonucleic acid (dsRNA), as well as compositions and methods for inhibiting the expression of the Factor VII gene in a cell or mammal using such dsRNA. The invention also provides compositions and methods for treating pathological conditions and diseases caused by expression of the Factor VII gene, such as coagulation disorders, including viral hemorrhagic fever. The dsRNA featured in the invention includes an RNA strand (the antisense strand) having a region that is less than 30 nucleotides in length, generally 19-24 nucleotides in length, and which is substantially complementary or fully complementary to the corresponding region of an mRNA transcript of the Factor VII gene.

In one embodiment, the invention provides double-stranded ribonucleic acid (dsRNA) molecules for inhibiting the expression of the Factor VII gene. The dsRNA includes at least two sequences that are complementary, e.g., substantially complementary, fully complementary, or sufficiently complementary to hybridize under physiological conditions, to each other. The dsRNA includes a sense strand including a first sequence and an antisense strand including a second sequence. The antisense strand includes a nucleotide sequence which is substantially or fully complementary to the corresponding region of an mRNA encoding Factor VII, and the region of complementarity is less than 30 nucleotides in length, generally 19-24 nucleotides, e.g., 19 to 21 nucleotides in length. In some embodiments, the dsRNA is from about 10 to about 15 nucleotides, and in other embodiments the dsRNA is from about 25 to about 30 nucleotides in length. In one embodiment the dsRNA, upon contacting with a cell expressing the Factor VII, inhibits the expression of the Factor VII gene by at least 25%, e.g., by at least 35%, or by at least 40%. In one embodiment, the Factor VII dsRNA is formulated in a stable nucleic acid particle (SNALP).

In one embodiment, the dsRNA can reduce mRNA levels by at least 40%, 60%, 80%, or 90%, e.g., as measured by an assay described herein. For example, the dsRNA can reduce liver Factor VII mRNA levels in rats by at least 40%, 60%, 80%, or 90%, such as with a single administration of a dose of 98N12-5 formulated Factor VII-targeting siRNA. In another embodiment, the dsRNA produces similar reduction in protein levels, e.g., as measured by an assay described herein. In yet another embodiment, a single injection of a 98N12-5 formulated Factor VII-targeting siRNA (siFVII) can mediate silencing for 1, 2, 3 or 4 weeks or more, e.g., as measured by an assay described herein. Assays to measure FVII mRNA and protein levels can also be performed by standard methods known in the art. For example, FVII mRNA can be measured by RT-PCR or Northern blot analysis. FVII protein levels can be measured by enzymatic assay, or by antibody-based methods, e.g., Western blot, ELISA, or immunohistochemistry.

The dsRNA molecules targeting FVII can include a first sequence of the dsRNA that is selected from the group consisting of the sense sequences of Tables 1, 2, and 3, and the second sequence is selected from the group consisting of the antisense sequences of Tables 1, 2, and 3. The dsRNA molecules featured in the invention can include naturally occurring nucleotides or can include at least one modified nucleotide, such as a 2'-O-methyl modified nucleotide, a nucleotide including a 5'-phosphorothioate group, and a terminal nucleotide linked to a cholesteryl derivative or dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, the first sequence of said dsRNA is selected from the group consisting of the sense sequences of Tables 1, 2, and 3, and the second sequence is selected from the group consisting of the antisense sequences of Tables 1, 2, and 3.

In another embodiment, the invention provides a cell including dsRNA targeting FVII. The cell is generally a mammalian cell, such as a human cell.

In another embodiment, the invention provides a pharmaceutical composition for inhibiting the expression of the Factor VII gene in an organism, including one or more of the dsRNA targeting FVII, and a pharmaceutically acceptable carrier.

In another embodiment, the invention provides a method for inhibiting the expression of the Factor VII gene in a cell, including the following steps:

(a) introducing into the cell a double-stranded ribonucleic acid (dsRNA), wherein the dsRNA includes at least two sequences that are complementary, e.g., substantially or fully complementary, to each other; and (b) maintaining the cell produced in step (a) for a time sufficient to obtain degradation of the mRNA transcript of the Factor VII gene, thereby inhibiting expression of the Factor VII gene in the cell.

The dsRNA includes a sense strand including a first sequence and an antisense strand including a second sequence. The antisense strand includes a region of complementarity which is substantially or fully complementary to the corresponding region of an mRNA encoding Factor VII, and where the region of complementarity is less than 30 nucleotides in length, generally 19-24 nucleotides in length, and where the dsRNA, upon contact with a cell expressing Factor VII, inhibits expression of the Factor VII gene by at least at least 40%. In one embodiment, the dsRNA can reduce mRNA by at least 40%, 60%, 80%, or 90%, e.g., as measured by an assay described herein. For example, the dsRNA can reduce liver Factor VII mRNA levels in rats by at least 40%, 60%, 80%, or 90% following a single administration of a dose of 98N12-5 formulated Factor VII-targeting siRNA. In one embodiment the dsRNA produce similar reductions in protein levels, e.g., as measured by an assay described herein. In another embodiment, a single injection of 98N12-5 formulated Factor VII-targeting siRNA (siFVII) can mediate silencing for 1, 2, 3 or 4 weeks or more, e.g., as measured by an assay described herein.

In another embodiment, the invention provides methods for treating, preventing or managing a Factor VII-mediated disorder by administering to a patient in need of such treatment, prevention or management a therapeutically or prophylactically effective amount of one or more of the dsRNAs featured in the invention.

In one embodiment, a FVII dsRNA can be used to treat a hemorrhagic fever, such as a viral hemorrhagic fever. Such a fever can be cause by a virus, such as a virus from the Filoviridae, Arenaviridae, Bunyaviridae, or Flaviridae families. For example, a FVII dsRNA can used to treat a hemorrhagic fever caused be a virus from the Filoviridae family, e.g., an Ebola or Marburg virus, or a virus from the Arenaviridae family, e.g., a Lassa virus.

In another embodiment, a FVII dsRNA featured herein is used to treat a coagulopathy or an inflammatory response, such as may be caused by a hemorrhagic fever.

In another embodiment, a FVII dsRNA can be used to treat a thrombotic disorder, e.g., a local thrombus, such as may arise from the rupture of atherosclerotic plaque. In another embodiment, administration of a FVII dsRNA is used to treat or prevent acute myocardial infarction or unstable angina. A FVII dsRNA can also be used to treat an occlusive coronary thrombus. In another embodiment, a FVII dsRNA is administered to treat or prevent deep vein thrombosis. In yet another embodiment, a FVII dsRNA is administered to treat or prevent a venous thromboembolism, e.g., in a cancer patients.

In another embodiment, a FVII dsRNA is administered to a patient, and after 1, 2, 3, or 4 weeks, the patient is tested to determine FVII mRNA levels, e.g., in the blood or urine, or in a particular tissue, e.g., the liver. If the level of FVII mRNA is determined to be above a pre-set level, the patient will be administered another dose of FVII dsRNA. If the level of FVII mRNA is determined to be below the pre-set level, the patient is not administered another dose of the FVII dsRNA. In yet another embodiment, a FVII dsRNA is administered to treat a proliferative disorder, e.g., cancer, such as ovarian, breast, head and neck, prostate, colorectal or lung cancer.

It has been discovered that a single administration can provide prolonged silencing. Thus, in another embodiment, a dose of FVII dsRNA is administered to a patient and the dose is sufficient that Factor VII mRNA or protein is: less than or equal to 20% of pretreatment levels (or the levels which would be seen in the absence of treatment) for at least 5, 10, or 15 days post-treatment; less than or equal to 40% of pretreatment levels (or the levels which would be seen in the absence of treatment) for at least 5, 10, or 15 days post-treatment; less than or equal to 60% of pretreatment levels (or the levels which would be seen in the absence of treatment) for at least 5, 10, 15, or 20 days post-treatment; less than or equal to 80% of pretreatment levels (or the levels which would be seen in the absence of treatment) for at least 5, 10, 15, 20, or 25 days post-treatment.

In one embodiment, a dose is administered and no additional dose of FVII dsRNA is administered for at least 5, 10, 15, 20, or 25 days after the first administration or course of administrations is finished.

In another embodiment, the invention provides vectors for inhibiting the expression of the Factor VII gene in a cell, including a regulatory sequence operably linked to a nucleotide sequence that encodes at least one strand of one of the dsRNA featured in the invention.

In another embodiment, the invention provides a cell including a vector for inhibiting the expression of the Factor VII gene in a cell. The vector includes a regulatory sequence operably linked to a nucleotide sequence that encodes at least one strand of one of the dsRNA featured in the invention.

TABLE 1

FVII dsRNAs (modified).

| Sense strand name | SEQ ID NO: | sequence (5'-3') | antisense strand name | SEQ ID NO: | sequence (5'-3') | duplex name |
|---|---|---|---|---|---|---|
| A26884 | 5 | GAcGcuGGccuucGuGcGcdTsdT | A26885 | 6 | GCGcACGAAGGCcAGCGUCdTsdT | AD16734 |
| A26886 | 7 | ccucuGccuGcccGAAcGGdTsdT | A26887 | 8 | CCGuuCGGGcAGGcAGAGGdTsdT | AD16735 |
| A26888 | 9 | ccuucGAGGGccGGAAcuGdTsdT | A26889 | 10 | cAGuuCCGGCCCUCGAAGGdTsdT | AD16736 |
| A26890 | 11 | ccAAccAcGAcAucGcGcudTsdT | A26891 | 12 | AGCGCGAuGUCGuGGuuGGdTsdT | AD16737 |
| A26892 | 13 | cucccAGuAcAucGAGuGGdTsdT | A26893 | 14 | CcACUCGAuGuACuGGGAGdTsdT | AD16738 |
| A26894 | 15 | cAAccAcGAcAucGcGcuGdTsdT | A26895 | 16 | cAGCGCGAuGUCGuGGuuGdTsdT | AD16739 |
| A26896 | 17 | cAGuccuAuAucuGcuucudTsdT | A26897 | 18 | AGAAGcAGAuAuAGGACuGdTsdT | AD16740 |
| A26898 | 19 | ccAuGGcAGGuccuGuuGudTsdT | A26899 | 20 | AcAAcAGGACCuGCcAuGGdTsdT | AD16741 |
| A26900 | 21 | cucuGccuGcccGAAcGGAdTsdT | A26901 | 22 | UCCGuuCGGGcAGGcAGAGdTsdT | AD16742 |
| A26902 | 23 | cGGcGGcuGuGAGcAGuAcdTsdT | A26903 | 24 | GuACuGCUcAcAGCCGCCGdTsdT | AD16743 |
| A26904 | 25 | uucuGuGccGGcuAcucGGdTsdT | A26905 | 26 | CCGAGuAGCCGGcAcAGAAdTsdT | AD16744 |
| A26906 | 27 | GAccAGcuccAGuccuAuAdTsdT | A26907 | 28 | uAuAGGAcuGGAGCuGGUCdTsdT | AD16745 |
| A26908 | 29 | uuGuuGGuGAAuGGAGcucdTsdT | A26909 | 30 | GAGCUCcAuucACcAAcAAdTsdT | AD16746 |
| A26910 | 31 | AuGuGGAAAAAuAccuAuudTsdT | A26911 | 32 | AAuAGGuAuuuuUCcAcAUdTsdT | AD16747 |
| A26912 | 33 | GuGGuccucAcuGAccAuGdTsdT | A26913 | 34 | cAuGGUcAGuGAGGACcACdTsdT | AD16748 |
| A26914 | 35 | AcGAcAucGcGcuGcuccGdTsdT | A26915 | 36 | CGGAGcAGCGCGAuGUCGUdTsdT | AD16749 |
| A26916 | 37 | cAAGGAccAGcuccAGuccdTsdT | A26917 | 38 | GGACuGGAGCuGGUCCuuGdTsdT | AD16750 |
| A26918 | 39 | GcAAGGAccAGcuccAGucdTsdT | A26919 | 40 | GACuGGAGCuGGUCCuuGCdTsdT | AD16751 |
| A26920 | 41 | AAGGAccAGcuccAGuccudTsdT | A26921 | 42 | AGGAcuGGAGCuGGUCCuudTsdT | AD16752 |
| A26922 | 43 | ccAGGGucucccAGuAcAudTsdT | A26923 | 44 | AuGuAcuGGGAGACCCuGGdTsdT | AD16753 |
| A26924 | 45 | cAuGGcAGGuccuGuuGuudTsdT | A26925 | 46 | AAcAAcAGGACCuGCcAuGdTsdT | AD16754 |
| A26926 | 47 | AcGGcGGcuGuGAGcAGuAdTsdT | A26927 | 48 | uACuGCUcAcAGCCGCCGUdTsdT | AD16755 |
| A26928 | 49 | cuGuGAGcAGuAcuGcAGudTsdT | A26929 | 50 | ACuGcAGuAcuGCUcAcAGdTsdT | AD16756 |
| A26930 | 51 | cGGuGcuGGGcGAGcAcGAdTsdT | A26931 | 52 | UCGuGCUCGCCcAGcACCGdTsdT | AD16757 |

"S" indicates a phosphorothioate linkage;
2'-O-Me modified nucleotides are indicated by lower case.

TABLE 2

FVII dsRNAs (unmodified).

| SEQ ID NO: | sense strand sequence (5'-3') | SEQ ID NO: | antisense strand sequence (5'-3') |
|---|---|---|---|
| 53 | GACGCUGGCCUUCGUGCGC | 54 | GCGCACGAAGGCCAGCGUC |
| 55 | CCUCUGCCUGCCCGAACGG | 56 | CCGUUCGGGCAGGCAGAGG |
| 57 | CCUUCGAGGGCCGGAACUG | 58 | CAGUUCCGGCCCUCGAAGG |
| 59 | CCAACCACGACAUCGCGCU | 60 | AGCGCGAUGUCGUGGUUGG |
| 61 | CUCCCAGUACAUCGAGUGG | 62 | CCACUCGAUGUACUGGGAG |
| 63 | CAACCACGACAUCGCGCUG | 64 | CAGCGCGAUGUCGUGGUUG |
| 65 | CAGUCCUAUAUCUGCUUCU | 66 | AGAAGCAGAUAUAGGACUG |
| 67 | CCAUGGCAGGUCCUGUUGU | 68 | ACAACAGGACCUGCCAUGG |
| 69 | CUCUGCCUGCCCGAACGGA | 70 | UCCGUUCGGGCAGGCAGAG |
| 71 | CGGCGGCUGUGAGCAGUAC | 72 | GUACUGCUCACAGCCGCCG |

TABLE 2-continued

FVII dsRNAs (unmodified).

| SEQ ID NO: | sense strand sequence (5'-3') | SEQ ID NO: | antisense strand sequence (5'-3') |
|---|---|---|---|
| 73 | UUCUGUGCCGGCUACUCGG | 74 | CCGAGUAGCCGGCACAGAA |
| 75 | GACCAGCUCCAGUCCUAUA | 76 | UAUAGGACUGGAGCUGGUC |
| 77 | UUGUUGGUGAAUGGAGCUC | 78 | GAGCUCCAUUCACCAACAA |
| 79 | AUGUGGAAAAAUACCUAUU | 80 | AAUAGGUAUUUUUCCACAU |
| 81 | GUGGUCCUCACUGACCAUG | 82 | CAUGGUCAGUGAGGACCAC |
| 83 | ACGACAUCGCGCUGCUCCG | 84 | CGGAGCAGCGCGAUGUCGU |
| 85 | CAAGGACCAGCUCCAGUCC | 86 | GGACUGGAGCUGGUCCUUG |
| 87 | GCAAGGACCAGCUCCAGUC | 88 | GACUGGAGCUGGUCCUUGC |
| 89 | AAGGACCAGCUCCAGUCCU | 90 | AGGACUGGAGCUGGUCCUU |
| 91 | CCAGGGUCUCCCAGUACAU | 92 | AUGUACUGGGAGACCCUGG |
| 93 | CAUGGCAGGUCCUGUUGUU | 94 | AACAACAGGACCUGCCAUG |
| 95 | ACGGCGGCUGUGAGCAGUA | 96 | UACUGCUCACAGCCGCCGU |
| 97 | CUGUGAGCAGUACUGCAGU | 98 | ACUGCAGUACUGCUCACAG |
| 99 | CGGUGCUGGGCGAGCACGA | 100 | UCGUGCUCGCCCAGCACCG |

TABLE 3

FVII dsRNAs (3' dinucleotide modifications).

| SEQ ID NO: | sense strand sequence (5'-3') | SEQ ID NO: | antisense strand sequence (5'-3') |
|---|---|---|---|
| 101 | GACGCUGGCCUUCGUGCGCNN | 102 | GCGCACGAAGGCCAGCGUCNN |
| 103 | CCUCUGCCUGCCCGAACGGNN | 104 | CCGUUCGGGCAGGCAGAGGNN |
| 105 | CCUUCGAGGGCCGGAACUGNN | 106 | CAGUUCCGGCCCUCGAAGGNN |
| 107 | CCAACCACGACAUCGCGCUNN | 108 | AGCGCGAUGUCGUGGUUGGNN |
| 109 | CUCCCAGUACAUCGAGUGGNN | 110 | CCACUCGAUGUACUGGGAGNN |
| 111 | CAACCACGACAUCGCGCUGNN | 112 | CAGCGCGAUGUCGUGGUUGNN |
| 113 | CAGUCCUAUAUCUGCUUCUNN | 114 | AGAAGCAGAUAUAGGACUGNN |
| 115 | CCAUGGCAGGUCCUGUUGUNN | 116 | ACAACAGGACCUGCCAUGGNN |
| 117 | CUCUGCCUGCCCGAACGGANN | 118 | UCCGUUCGGGCAGGCAGAGNN |
| 119 | CGGCGGCUGUGAGCAGUACNN | 120 | GUACUGCUCACAGCCGCCGNN |
| 121 | UUCUGUGCCGGCUACUCGGNN | 122 | CCGAGUAGCCGGCACAGAANN |
| 123 | GACCAGCUCCAGUCCUAUANN | 124 | UAUAGGACUGGAGCUGGUCNN |
| 125 | UUGUUGGUGAAUGGAGCUCNN | 126 | GAGCUCCAUUCACCAACAANN |
| 127 | AUGUGGAAAAAUACCUAUUNN | 128 | AAUAGGUAUUUUUCCACAUNN |
| 129 | GUGGUCCUCACUGACCAUGNN | 130 | CAUGGUCAGUGAGGACCACNN |
| 131 | ACGACAUCGCGCUGCUCCGNN | 132 | CGGAGCAGCGCGAUGUCGUNN |
| 133 | CAAGGACCAGCUCCAGUCCNN | 134 | GGACUGGAGCUGGUCCUUGNN |
| 135 | GCAAGGACCAGCUCCAGUCNN | 136 | GACUGGAGCUGGUCCUUGCNN |
| 137 | AAGGACCAGCUCCAGUCCUNN | 138 | AGGACUGGAGCUGGUCCUUNN |
| 139 | CCAGGGUCUCCCAGUACAUNN | 140 | AUGUACUGGGAGACCCUGGNN |
| 141 | CAUGGCAGGUCCUGUUGUUNN | 142 | AACAACAGGACCUGCCAUGNN |
| 143 | ACGGCGGCUGUGAGCAGUANN | 144 | UACUGCUCACAGCCGCCGUNN |
| 145 | CUGUGAGCAGUACUGCAGUNN | 146 | ACUGCAGUACUGCUCACAGNN |
| 147 | CGGUGCUGGGCGAGCACGANN | 148 | UCGUGCUCGCCCAGCACCGNN |

N indicates any nucleotide (G, A, C, T)

The details of one or more embodiments of the invention are set forth in the description below. Other features, objects, and advantages of the invention will be apparent from the description and the drawings, and from the claims.

DETAILED DESCRIPTION

Figure 1:
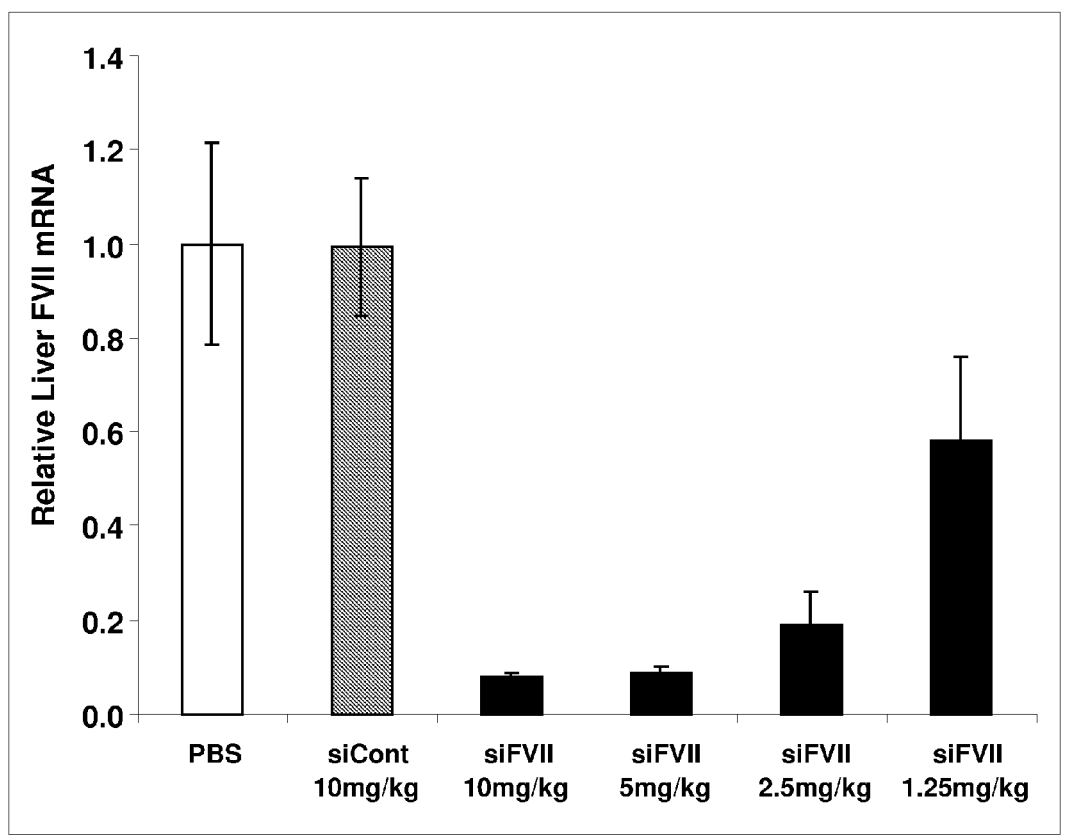
FIG. 1 is a bar graph showing liver FVII mRNA levels following administration of FVII siRNA.

The invention provides double-stranded ribonucleic acid (dsRNA), as well as compositions and methods for inhibiting the expression of the Factor VII gene in a cell or mammal using the dsRNA. The invention also provides compositions and methods for treating pathological conditions and diseases in a mammal caused by the expression of the Factor VII gene using dsRNA. dsRNA directs the sequence-specific degradation of mRNA through a process known as RNA interference (RNAi). The process occurs in a wide variety of organisms, including mammals and other vertebrates.

The dsRNA featured in the invention includes an RNA strand (the antisense strand) having a region which is less than 30 nucleotides in length, generally 19-24 nucleotides in length, and is substantially or fully complementary to at least part of an mRNA transcript of the Factor VII gene. The use of these dsRNAs enables the targeted degradation of mRNAs of genes that are implicated in thrombosis in mammals. Using cell-based and animal assays, the present inventors have demonstrated that very low dosages of these dsRNA can specifically and efficiently mediate RNAi, resulting in significant inhibition of expression of the Factor VII gene. Thus, the methods and compositions featured in the invention include dsRNAs useful for treating a thrombotic disorder.

The following detailed description discloses how to make and use the dsRNA and compositions containing dsRNA to inhibit the expression of a target Factor VII gene, as well as compositions and methods for treating diseases and disorders caused by the expression of Factor VII, such as a thrombotic disorder. The pharmaceutical compositions featured in the invention include a dsRNA having an antisense strand having a region of complementarity which is less than 30 nucleotides in length, generally 19-24 nucleotides in length, and is substantially complementary to at least part of an RNA transcript of the Factor VII gene, together with a pharmaceutically acceptable carrier.

Accordingly, certain aspects of the invention provide pharmaceutical compositions including a dsRNA targeting FVII, together with a pharmaceutically acceptable carrier, methods of using the compositions to inhibit expression of the Factor VII gene, and methods of using the pharmaceutical compositions to treat diseases caused by expression of the Factor VII gene.

I. DEFINITIONS

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide including a nucleotide bearing such replacement moiety. For example, without limitation, a nucleotide including inosine as its base may base pair with nucleotides containing adenine, cytosine, or uracil. Hence, nucleotides containing uracil, guanine, or adenine may be replaced in the nucleotide sequences featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences including such replacement moieties are embodiments featured in the invention.

By "Factor VII" as used herein is meant a Factor VII mRNA, protein, peptide, or polypeptide. The term "Factor VII" is also known in the art as AI132620, Cf7, Coagulation factor VII precursor, coagulation factor VII, FVII, Serum prothrombin conversion accelerator, FVII coagulation protein, and eptacog alfa.

As used herein, "target sequence" refers to a contiguous portion of the nucleotide sequence of an mRNA molecule formed during the transcription of the Factor VII gene, including mRNA that is a product of RNA processing of a primary transcription product.

As used herein, the term "strand including a sequence" refers to an oligonucleotide including a chain of nucleotides that is described by the sequence referred to using the standard nucleotide nomenclature.

As used herein, and unless otherwise indicated, the term "complementary," when used in the context of a nucleotide pair, means a classic Watson-Crick pair, i.e., GC, AT, or AU. It also extends to classic Watson-Crick pairings where one or both of the nucleotides has been modified as described herein, e.g., by a rbose modification or a phosphate backpone modification. It can also include pairing with an inosine or other entity that does not substantially alter the base pairing properties.

As used herein, and unless otherwise indicated, the term "complementary," when used to describe a first nucleotide sequence in relation to a second nucleotide sequence, refers to the ability of an oligonucleotide or polynucleotide including the first nucleotide sequence to hybridize and form a duplex structure under certain conditions with an oligonucleotide or polynucleotide including the second nucleotide sequence, as will be understood by the skilled person. Complementarity can include, full complementarity, substantial complementarity, and sufficient complementarity to allow hybridization under physiological conditions, e.g, under physiologically relevant conditions as may be encountered inside an organism. Full complementarity refers to complementarity, as defined above for an individual pair, at all of the pairs of the first and second sequence. When a sequence is "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. Substantial complementarity can also be defined as hybridization under stringent conditions, where stringent conditions may include: 400 mM NaCl, 40 mM PIPES pH 6.4, 1 mM EDTA, 50° C. or 70° C. for 12-16 hours followed by washing. The skilled person will be able to determine the set of conditions most appropriate for a test of complementarity of two sequences in accordance with the ultimate application of the hybridized nucleotides.

However, where two oligonucleotides are designed to form, upon hybridization, one or more single stranded overhangs, such overhangs shall not be regarded as mismatches with regard to the determination of complementarity. For example, a dsRNA including one oligonucleotide 21 nucleotides in length and another oligonucleotide 23 nucleotides in length, wherein the longer oligonucleotide includes a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary", "substantially complementary" and sufficient complementarity to allow hybridization under physiological conditions, e.g, under physiologically relevant conditions as may be encountered inside an organism, may be used herein with respect to the base matching between the sense strand and the antisense strand of a dsRNA, or between the antisense strand of a dsRNA and a target sequence, as will be understood from the context of their use.

As used herein, a polynucleotide which is "complementary, e.g., substantially complementary to at least part of" a messenger RNA (mRNA) refers to a polynucleotide which is complementary, e.g., substantially complementary, to a contiguous portion of the mRNA of interest (e.g., encoding Factor VII). For example, a polynucleotide is complementary to at least a part of a Factor VII mRNA if the sequence is substantially complementary to a non-interrupted portion of an mRNA encoding Factor VII.

The term "double-stranded RNA" or "dsRNA", as used herein, refers to a ribonucleic acid molecule, or complex of ribonucleic acid molecules, having a duplex structure including two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as a "small inhibitory RNA," "siRNA," "iRNA agent" or "RNAi agent."

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov, M. and Devereux, J., eds., M. Stockton Press, New York (1991)). "Substantially identical," as used herein, means there is a very high degree of homology (e.g., 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. The dsRNA is typically 100% complementary to the target RNA, but in some embodiments, the dsRNA may contain single or multiple base-pair random mismatches between the RNA and the target gene.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed. SNALPs are described, e.g., in U.S. Patent Application Publication Nos. 20060240093, 20070135372, and U.S. Ser. No. 61/045,228 filed Apr. 15, 2008. These applications are hereby incorporated by reference.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of," in as far as they refer to the Factor VII gene, herein refer to the at least partial suppression of the expression of the Factor VII gene, as manifested by a reduction of the amount of mRNA transcribed from the Factor VII gene which may be isolated from a first cell or group of cells in which the Factor VII gene is transcribed and which has or have been treated such that the expression of the Factor VII gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in controls cells})} \cdot 100\%$$

Alternatively, the degree of inhibition may be given in terms of a reduction of a parameter that is functionally linked to Factor VII gene transcription, e.g. the amount of protein encoded by the Factor VII gene which is secreted by a cell, or the number of cells displaying a certain phenotype, e.g apoptosis. In principle, Factor VII gene silencing may be determined in any cell expressing the target, either constitutively or by genomic engineering, and by any appropriate assay. However, when a reference is needed in order to determine whether a given siRNA inhibits the expression of the Factor VII gene by a certain degree and therefore is encompassed by the instant invention, the assays provided in the Examples below shall serve as such reference.

For example, in certain instances, expression of the Factor VII gene is suppressed by at least about 20%, 25%, 35%, 40% or 50% by administration of the double-stranded oligonucleotide featured in the invention. In some embodiments, the Factor VII gene is suppressed by at least about 60%, 70%, or 80% by administration of the double-stranded oligonucleotide. In other embodiments, the Factor VII gene is suppressed by at least about 85%, 90%, or 95% by administration of the double-stranded oligonucleotide.

The terms "treat", "treatment," and the like, refer to relief from or alleviation of a disease or disorder, such as a viral hemorrhagic fever. In the context of the present invention insofar as it relates to any of the other conditions recited herein below (e.g., a Factor VII-mediated condition other than a thrombotic disorder), the terms "treat," "treatment," and the like mean to relieve or alleviate at least one symptom associated with such condition, or to slow or reverse the progression of such condition.

As used herein, the term "Factor VII-mediated condition or disease" and related terms and phrases refer to a condition or disorder characterized by inappropriate, e.g., greater than normal, Factor VII activity. Inappropriate Factor VII functional activity might arise as the result of Factor VII expression in cells which normally do not express Factor VII, or increased Factor VII expression (leading to, e.g., a symptom of a viral hemorrhagic fever, or a thrombus). A Factor VII-mediated condition or disease may be completely or partially mediated by inappropriate Factor VII functional activity. However, a Factor VII-mediated condition or disease is one in which modulation of Factor VII results in some effect on the underlying condition or disorder (e.g., a Factor VII inhibitor results in some improvement in patient well-being in at least some patients).

A "hemorrhagic fever" includes a combination of illnesses caused by a viral infection. Fever and gastrointestinal symptoms are typically followed by capillary hemorrhaging.

A "coagulopathy" is any defect in the blood clotting mechanism of a subject.

As used herein, a "thrombotic disorder" is any disorder characterized by unwanted blood coagulation.

As used herein, the phrases "therapeutically effective amount" and "prophylactically effective amount" refer to an amount that provides a therapeutic benefit in the treatment, prevention, or management of a viral hemorrhagic fever, or an overt symptom of such disorder, e.g., hemorraging, fever, weakness, muscle pain, headache, inflammation, or circulatory shock. The specific amount that is therapeutically effective can be readily determined by ordinary medical practitioner, and may vary depending on factors known in the art, such as, e.g. the type of thrombotic disorder, the patient's history and age, the stage of the disease, and the administration of other agents.

As used herein, a "pharmaceutical composition" includes a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. DOUBLE-STRANDED RIBONUCLEIC ACID (dsRNA)

In one embodiment, the invention provides double-stranded ribonucleic acid (dsRNA) molecules for inhibiting the expression of the Factor VII gene in a cell or mammal. The dsRNA includes an antisense strand including a region of complementarity which is complementary to the corresponding region of an mRNA formed in the expression of the Factor VII gene, and wherein the region of complementarity is less than 30 nucleotides in length, generally 19-24 nucleotides in length. In one embodiment the dsRNA, upon contact with a cell expressing said Factor VII gene, inhibits the expression of said Factor VII gene, e.g., in a cell-based assay, by at least 25%, e.g., by at least 40%. The dsRNA includes two RNA strands that are sufficiently complementary to hybridize to form a duplex structure. The sense strand includes a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 21 and 23 base pairs in length. Similarly, the region of complementarity to the target sequence is between 15 and 30, more generally between 18 and 25, yet more generally between 19 and 24, and most generally between 21 and 23 nucleotides in length. The dsRNA targeting FVII may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In one embodiment, the Factor VII gene is the human Factor VII gene. In specific embodiments, the first sequence is selected from the group consisting of the sense sequences of Tables 1, 2, and 3, and the second sequence is selected from the group consisting of the antisense sequences of Tables 1, 2, and 3. In one embodiment, the cleavage is within 6, 5, 4, 3, 2 or 1 nucleotides of the cleavage site for a dsRNA from Tables 1, 2, and 3.

In further embodiments, the dsRNA includes at least one nucleotide sequence selected from the groups of sequences provided in Tables 1, 2, and 3. In other embodiments, the dsRNA includes at least two sequences selected from this group, wherein one of the at least two sequences is complementary to another of the at least two sequences, and one of the at least two sequences is substantially complementary to a sequence of an mRNA generated in the expression of the Factor VII gene. Generally, the dsRNA includes two oligonucleotides, wherein one oligonucleotide is described as the sense strand in Tables 1, 2, or 3, and the second oligonucleotide is described as the antisense strand in Tables 1, 2, or 3.

The skilled person is well aware that dsRNAs including a duplex structure of between 20 and 23, but specifically 21, base pairs have been identified as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1, 2, and 3, the dsRNAs featured in the invention can comprise at least one strand of a length of minimally 21 nt. It can be reasonably expected that shorter dsRNAs including one of the sequences of Tables 1, 2 or 3 minus only a few nucleotides on one or both ends may be similarly effective as compared to the dsRNAs described above. Hence, dsRNAs including a partial sequence of at least 15, 16, 17, 18, 19, 20, or more contiguous nucleotides from one of the sequences of Tables 1, 2, or 3, and differing in their ability to inhibit the expression of the Factor VII gene in a FACS assay as described herein below by not more than 5, 10, 15, 20, 25, or 30% inhibition from a dsRNA including the full sequence, are contemplated by the invention.

In addition, the dsRNAs provided in Tables 1, 2, and 3 identify selected sites in the Factor VII mRNA that are susceptible to RNAi based cleavage. As such, the invention further includes dsRNAs that target within the sequence targeted by one of the agents of the present invention. As used herein, a second dsRNA is said to target within the sequence of a first dsRNA if the second dsRNA cleaves the message anywhere within the mRNA that is complementary to the antisense strand of the first dsRNA. Such a second agent will generally consist of at least 15 contiguous nucleotides from one of the sequences provided in Tables 1, 2, or 3 coupled to additional nucleotide sequences taken from the region contiguous to the selected sequence in the Factor VII gene.

The dsRNA featured in the invention can contain one or more mismatches to the target sequence. In one embodiment, the dsRNA contains no more than 3 mismatches. If the antisense strand of the dsRNA contains mismatches to a target sequence, the area of mismatch is typically not located in the center of the region of complementarity. If the antisense strand of the dsRNA contains mismatches to the target sequence, then the mismatch is typically restricted to 5 nucleotides from either end, for example 5, 4, 3, 2, or 1 nucleotide from either the 5' or 3' end of the region of complementarity. For example, for a 23 nucleotide dsRNA strand that is complementary to a region of the Factor VII gene, the dsRNA generally does not contain any mismatch within the central 13 nucleotides. The methods described herein can be used to determine whether a dsRNA containing a mismatch to a target sequence is effective in inhibiting the expression of the Factor VII gene. Consideration of the efficacy of dsRNAs with mismatches in inhibiting expression of the Factor VII gene is important, especially if the particular region of complementarity in the Factor VII gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has 1-10 nucleotide overhangs each at the 3' end and the 5' end over the sense strand. In one embodiment, the sense strand of the dsRNA has 1-10 nucleotides overhangs each at the 3' end and the 5' end over the antisense strand. In another embodiment, one or more of the nucleotides in the overhang is replaced with a nucleoside thiophosphate.

In yet another embodiment, the dsRNA is chemically modified to enhance stability. For example, the nucleic acids of the dsRNAs targeting FVII may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of dsRNA compounds include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Typical modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Typical modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other typical dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In typical embodiments, dsRNAs have phosphorothioate backbones and oligonucleosides with heteroatom backbones, and in particular $—CH_2—NH—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$ [wherein the native phosphodiester backbone is represented as $—O—P—O—CH_2—$] of the above-referenced U.S. Pat. No. 5,489,677, and the amide backbones of the above-referenced U.S. Pat. No. 5,602,240. In other embodiments, the dsRNAs featured in the invention have morpholino backbone structures of the above-referenced U.S. Pat. No. 5,034,506.

Modified dsRNAs may also contain one or more substituted sugar moieties. Typical dsRNAs include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Typical modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. In one embodiment, the modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. In other embodiments, modifications include 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., Eds., DsRNA Research and Applications, CRC Press, Boca Raton, 1993, pp. 276-278) and represent typical base substitutions, particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs targeting FVII involves chemical linkage of the dsRNA to one or more moieties or conjugates that enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-S-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate. The use of a cholesterol conjugate, for example, can increase targeting vaginal epithelium cells, a site of Factor VII expression expression.

Vector Encoded RNAi Agents

The dsRNAs targeting FVII can also be expressed from recombinant viral vectors intracellularly in vivo. For example, recombinant viral vectors can include sequences encoding the dsRNA and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors can also include inducible or regulatable promoters for expression of the dsRNA in a particular tissue or in a particular intracellular environment. The use of recombinant viral vectors to deliver dsRNA to cells in vivo is discussed in more detail below.

dsRNA targeting FVII can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Typical viral vectors are those derived from AV and AAV. In one embodiment, the dsRNA targeting FVII is expressed as two separate, complementary single-stranded RNA molecules from a recombinant AAV vector including, for example, either the U6 or H1 RNA promoters, or the cytomegalovirus (CMV) promoter.

A suitable AV vector for expressing a dsRNA targeting FVII, a method for constructing the recombinant AV vector, and a method for delivering the vector into target cells, are described in Xia H et al. (2002), Nat. Biotech. 20: 1006-1010.

Suitable AAV vectors for expressing the dsRNA targeting FVII, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

III. PHARMACEUTICAL COMPOSITIONS INCLUDING dsRNA

In one embodiment, the invention provides pharmaceutical compositions including a dsRNA, as described herein, and a pharmaceutically acceptable carrier. The pharmaceutical composition including the dsRNA is useful for treating a disease or disorder associated with the expression or activity of the Factor VII gene, such as pathological processes mediated by Factor VII expression. Such pharmaceutical compositions are formulated based on the mode of delivery. One example is compositions that are formulated for systemic administration via parenteral delivery.

The pharmaceutical compositions featured in the invention are administered in dosages sufficient to inhibit expression of the Factor VII gene. The present inventors have found that, because of their improved efficiency, compositions including the dsRNAs targeting FVII can be administered at surprisingly low dosages. A maximum dosage of 5 mg dsRNA per kilogram body weight (e.g., 1 mg/kg, 1.5 mg/kg, 2 mg/kg, 2.5 mg/kg, 3 mg/kg, 3.5 mg/kg, 4 mg/kg, 4.5 mg/kg) of recipient per day is sufficient to inhibit or completely suppress expression of the Factor VII gene.

In general, a suitable dose of dsRNA will be in the range of 0.01 to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for vaginal delivery of agents, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by Factor VII expression. Such models are used for in vivo testing of dsRNA, as well as for determining a therapeutically effective dose.

The present invention also includes pharmaceutical compositions and formulations which include the dsRNA compounds targeting FVII. The pharmaceutical compositions may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal), oral or parenteral. Administration may also be designed to result in preferential localization to particular tissues through local delivery, e.g. by direct intraarticular injection into joints, by rectal administration for direct delivery to the gut and intestines, by intravaginal administration for delivery to the cervix and vagina, by intravitreal administration for delivery to the eye. Parenteral administration includes intravenous, intraarterial, intraarticular, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Topical formulations include those in which the dsRNAs are in admixture with a topical delivery agent such as lipids, liposomes, fatty acids, fatty acid esters, steroids, chelating agents and surfactants. Typical lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). DsRNAs may be encapsulated within liposomes or may form complexes thereto, in particular to cationic liposomes. Alternatively, dsRNAs may be complexed to lipids, in particular to cationic lipids. Typical fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315, 298 filed on May 20, 1999 which is incorporated herein by reference in its entirety.

In one embodiment, a FVII dsRNA featured in the invention is fully encapsulated in the lipid formulation (e.g., to form a SPLP, pSPLP, SNALP, or other nucleic acid-lipid particle). As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), or a mixture thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4 HCl (MW 1487) (Formula I), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/mL; Cholesterol, 25 mg/mL, PEG-Ceramide C16, 100 mg/mL. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. LipidsiRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

chelators. Typical surfactants include fatty acids and/or esters or salts thereof, bile acids and/or salts thereof. Typical bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Typical fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylaza- Formula 1

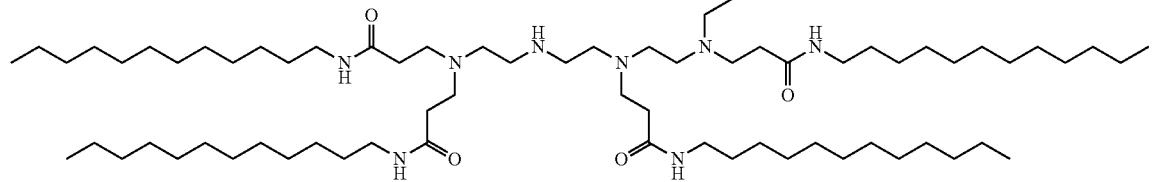

ND98 Isomer I

LNP01 formulations are described, e.g., in International Application Publication No. WO 2008/042973, which is hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Typical oral formulations are those in which dsRNAs are administered in conjunction with one or more penetration enhancers surfactants and cycloheptan-2-one, an acylcarnitine, an acylcholine, or a monoglyceride, a diglyceride or a pharmaceutically acceptable salt thereof (e.g. sodium). In some embodiments, formulations include combinations of penetration enhancers, for example, fatty acids/salts in combination with bile acids/salts. In one embodiment, the combination is the sodium salt of lauric acid, capric acid and UDCA. Further penetration enhancers include polyoxyethylene-9-lauryl ether, polyoxyethylene-20-cetyl ether. DsRNAs targeting FVII may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Typical complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108, 673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 .mu.m in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems including two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems including non-ionic surfactant and cholesterol. Non-ionic liposomal formulations including Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes including one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) includes one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes including one or more glycolipids are known in the art. Papahadjopoulos et al. (Ann. N.Y. Acad. Sci., 1987, 507, 64) reported the ability of monosialoganglioside GM1, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes including (1) sphingomyelin and (2) the ganglioside GM1 or a galactocerebroside sulfate ester. U.S. Pat. No. 5,543,152 (Webb et al.) discloses liposomes including sphingomyelin. Liposomes including 1,2-sn-dimyristoylphosphat-idylcholine are disclosed in WO 97/13499 (Lim et al.).

Many liposomes including lipids derivatized with one or more hydrophilic polymers, and methods of preparation thereof, are known in the art. Sunamoto et al. (Bull. Chem. Soc. Jpn., 1980, 53, 2778) described liposomes including a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes including phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes including a number of other lipid-polymer conjugates are disclosed in WO 91/05545 and U.S. Pat. No. 5,225,212 (both to Martin et al.) and in WO 94/20073 (Zalipsky et al.) Liposomes including PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes including nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA RNA. U.S. Pat. No. 5,665,710 to Rahman et al. describes certain methods of encapsulating oligodeoxynucleotides in liposomes. WO 97/04787 to Love et al. discloses liposomes including dsRNA dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carryier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments featured in the invention provide pharmaceutical compositions containing (a) one or more dsRNA molecules and (b) one or more other therapeutic agents which function by a non-dsRNA-mediated mechanism. For example, the one or more other therapeutic agents include anticoagulants. Exemplary anticoagulants include, e.g., Warfarin (COUMADIN™); LMWH (Low Molecular Weight Heparins); factor Xa inhibitors, e.g, bisamidine compounds, and phenyl and naphthylsulfonamides; unfractionated heparin; aspirin; and platelet glycoprotein IIb/IIIa blockers.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Suitable compounds typically exhibit high therapeutic indices.

The data obtained from cell culture assays and animal studies can be used in formulation a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the method featured herein, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs targeting FVII can be administered in combination with other known agents effective in treatment of pathological processes mediated by Factor VII expression. In any event, the administering physician can adjust the amount and timing of dsRNA administration on the basis of results observed using standard measures of efficacy known in the art or described herein.

Methods for Treating Diseases Caused by Expression of the Factor VII Gene

In one embodiment, the invention provides a method for treating a subject having a pathological condition mediated by the expression of the Factor VII gene, such as a viral hemorrhagic fever. In this embodiment, the dsRNA acts as a therapeutic agent for controlling the expression of the Factor VII protein. The method includes administering a pharmaceutical composition to the patient (e.g., human), such as a patient infected with a virus, such that expression of the Factor VII gene is silenced. Because of their high specificity, the dsRNAs featured in the invention specifically target mRNAs of the Factor VII gene.

As used herein, the term "Factor VII-mediated condition or disease" and related terms and phrases refer to a condition or disorder characterized by unwanted or inappropriate, e.g., abnormal Factor VII activity. Inappropriate Factor VII functional activity might arise as the result of Factor VII expression in cells which normally do not express Factor VII, or increased Factor VII expression and/or activity (leading to, e.g., a symptom of a viral hemorrhagic fever, or a thrombotic disorder). A Factor VII-mediated condition or disease may be completely or partially mediated by inappropriate Factor VII functional activity which may result by way of inappropriate activation of Factor VII. Regardless, a Factor VII-mediated condition or disease is one in which modulation of Factor VII via RNA interference results in some effect on the underlying condition or disorder (e.g., a Factor VII inhibitor results in some improvement in patient well-being in at least some patients).

The anti-Factor VII dsRNAs of the present invention may be used to treat or diagnose a viral hemorrhagic fever in a subject. Treatment methods include administering to a subject an anti-Factor VII dsRNA describe herein in an amount effective to treat the hemorrhagic fever.

Pathological processes refer to a category of biological processes that produce a deleterious effect. For example, unregulated expression of Factor VII is associated with viral hemorrhagic fever, thrombotic disorders and cancer. A compound featured in the invention can typically modulate a pathological process when the compound reduces the degree or severity of the process. For example, a hemorrhagic fever can be prevented, or related pathological processes can be modulated, by the administration of a dsRNA that reduces or otherwise modulates the expression of or at least one activity of Factor VII.

The dsRNA molecules featured herein may therefore also be used to treat or prevent a viral hemorrhagic fever. The dsRNA can treat or prevent a hemorrhagic fever by ameliorating and/or preventing coagulopathy or an inflammatory response.

The dsRNA molecules featured herein may also be used to treat a thrombotic disorder. Thrombotic disorders that can be treated with a dsRNA that targets Factor VII include, but are not limited to, a local thrombus, acute myocardial infarction, unstable angina, an occlusive coronary thrombus, or deep vein thrombosis.

The pharmaceutical compositions encompassed by the invention may be administered by any means known in the art including, but not limited to oral or parenteral routes, including intravenous, intramuscular, intraarticular, intraperitoneal, subcutaneous, intravitreal, transdermal, airway (aerosol), nasal, rectal, vaginal and topical (including buccal and sublingual) administration, and epidural administration. In some embodiments, the pharmaceutical compositions are administered intraveneously by infusion or injection.

Methods for Inhibiting Expression of the Factor VII Gene

In yet another aspect, the invention provides a method for inhibiting the expression of the Factor VII gene in a mammal. The method includes administering a composition featured in the invention to the mammal such that expression of the target Factor VII gene is silenced. Because of their high specificity, the dsRNAs featured in the invention specifically target RNAs (primary or processed) of the target Factor VII gene. Compositions and methods for inhibiting the expression of the Factor VII gene using dsRNAs can be performed as described elsewhere herein.

In one embodiment, the method includes administering a composition including a dsRNA, wherein the dsRNA includes a nucleotide sequence that is complementary to at least a part of an RNA transcript of the Factor VII gene of the mammal to be treated. When the organism to be treated is a mammal such as a human, the composition may be administered by any means known in the art including, but not limited to oral or parenteral routes, including intravenous, intramuscular, intraarticular, intracranial, subcutaneous, intravitreal, transdermal, airway (aerosol), nasal, rectal, vaginal and topical (including buccal and sublingual) administration. In certain embodiments, the compositions are administered by intraveneous infusion or injection.

dsRNA Expression Vectors

In another aspect, FVII specific dsRNA molecules that modulate FVII gene expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol*. (1992) 158:97-129)); adenovirus (see, for example, Berkner, et al., *BioTechniques* (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Factor VII gene or multiple Factor VII genes over a period of a week or more are also contemplated by the invention. Successful introduction of the vectors into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The Factor VII specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Design of siRNA to Target FVII siRNA design was performed to identify siRNAs targeting coagulation factor VII (also known as AI132620, Cf7, Coagulation factor VII precursor, coagulation factor VII, FVII, Serum prothrombin conversion accelerator, FVII coagulation protein, and eptacog alfa).

Human mRNA sequences to two FVII transcript variants, RefSeq ID number: NM_000131.3 (3141 bp) (see, e.g., FIGS. 7A and 7B) and NM_019616.2 (3075 bp) (GenBank record dated Nov. 18, 2007) (see, e.g., FIGS. 8A and 8B), were used. Rhesus sequences were assembled from NCBI and ENSEMBL database sources (see below).

siRNA duplexes cross-reactive to human and rhesus monkey (Macaca mulatta) FVII with predicted specificity to human FVII were designed. Twenty-four duplexes were synthesized for screening, and these are shown in Table 1.

Human-rhesus cross-reactivity. Human-rhesus cross-reactivity was defined as prerequisite for in silico selection of siRNAs. For this, it was assured that two curated human variants for FVII and available rhesus sequences contained 19mer siRNA target sites.

Human mRNA sequences to two FVII transcript variants were downloaded from NCBI Nucleotide database; one of these, NM_000131.3, was further used as the reference sequence.

Sequences for rhesus FVII mRNAs downloaded from the NCBI Nucleotide database (NM_001080136.1-2424 bp and D21212.1-478 bp, partial cds), and ENSEMBL database (ENSMMUT00000001477-1389 bp and ENSMMUT00000042997-1326 bp) were aligned to build a consensus sequence for rhesus monkey FVII with a total length of 2424 bp.

All possible 19 mers were extracted from the human mRNA reference sequence, resulting in a pool of candidate target sites corresponding to 3122 (sense strand) sequences of NM_000131.3-reactive FVII siRNAs.

To determine siRNAs reactive towards both curated human variants and the consensus rhesus sequences, each candidate siRNA target site was searched in the human RefSeq sequence NM_019616.2 and the partial rhesus sequence. The resulting siRNAs were defined as human-rhesus cross-reactive siRNAs.

Specificity prediction. The predicted specificity of the siRNA was used as criterion for final selection, manifested by targeting human FVII mRNA sequences, but not other human mRNAs.

To identify human FVII-specific siRNAs that will avoid targeting non-FVII human transcripts (potential "off-target" genes), human-rhesus cross-reactive siRNAs were subjected to a homology search against the human RefSeq mRNA database which was considered to represent the comprehensive human transcriptome.

For this, the fastA algorithm was used to determine the most homologous hit region for antisense and sense strands to each sequence of the human RefSeq database (release 24).

Resulting alignments with every RefSeq entry were further analyzed by a perl script to extract the number and position of mismatches, and based on this, to calculate a specificity score.

siRNA strands were assigned a category of specificity according to the calculated specificity scores: a score above three qualified as highly specific, equal to three as specific, and between 2.2 and 2.8 as moderate specific.

siRNA sequence selection. For selection of siRNAs, a specificity score of 2.8 or more for the antisense strand, and 2 or more for the sense strand, was chosen as a prerequisite for selection of siRNAs, whereas all sequences containing four or more consecutive G's (poly-G sequences) were excluded.

Twenty-four siRNA sequences, cross-reactive to all human and rhesus monkey FVII mRNAs mentioned above, and passing the specificity criterion, were selected (see Table 1). The resulting set of twenty-four consists of two highly specific, 16 specific, and six moderately specific siRNAs (considering specificity of the antisense strand only).

Example 2

Silencing of FVII In Vivo

Rats (n=4) were given a single i.v. injection of siFVII formulated with the lipidoid formulation 98N12-5 at doses of 1.25, 2.5, 3, 3.5, 4, 5, and 10 mg/kg.

Figure 2:
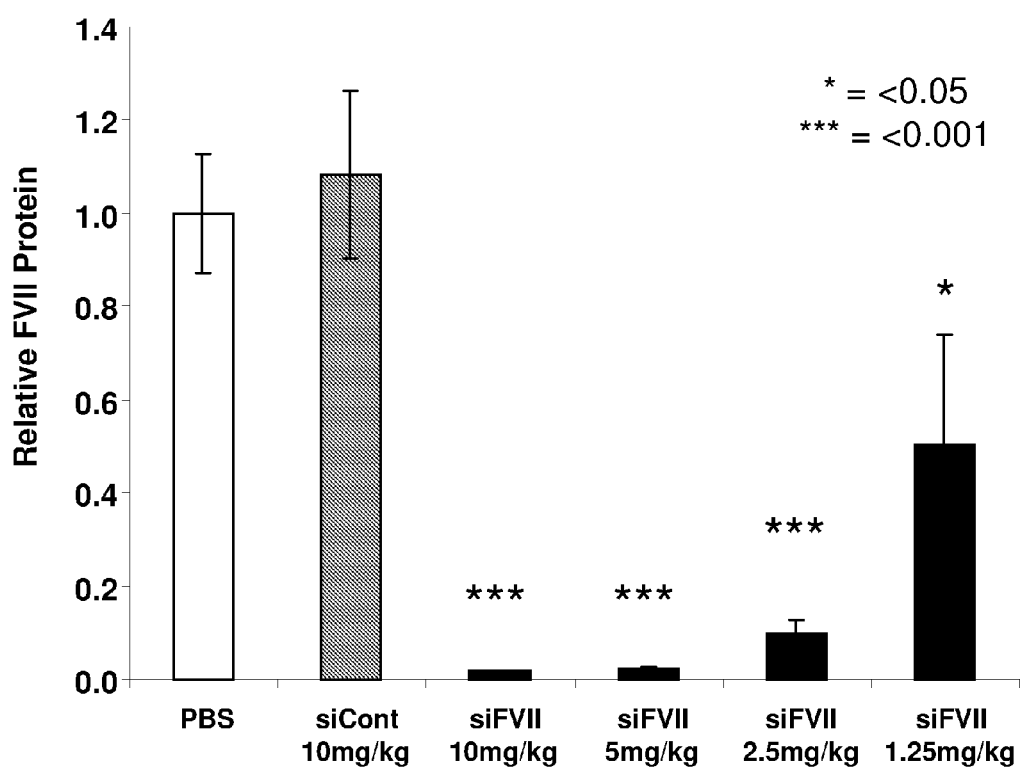
FIG. 2 is a bar graph showing serum FVII protein levels following administration of FVII siRNA.

Animals were bled and sacrificed 48 h after administration. Significant, dose-dependent reductions in liver Factor VII mRNA levels were observed, with 40%, 80%, and greater than 90% silencing at 1.25, 2.5, and 5 mg/kg, respectively (FIG. 1). No silencing was observed using a formulated control siRNA (siCont), demonstrating specificity of silencing. The reduction in liver Factor VII mRNA levels produced a concomitant dose-dependent reduction in serum Factor VII protein levels, with nearly complete silencing at the highest dose levels (FIG. 2).

Figure 3:
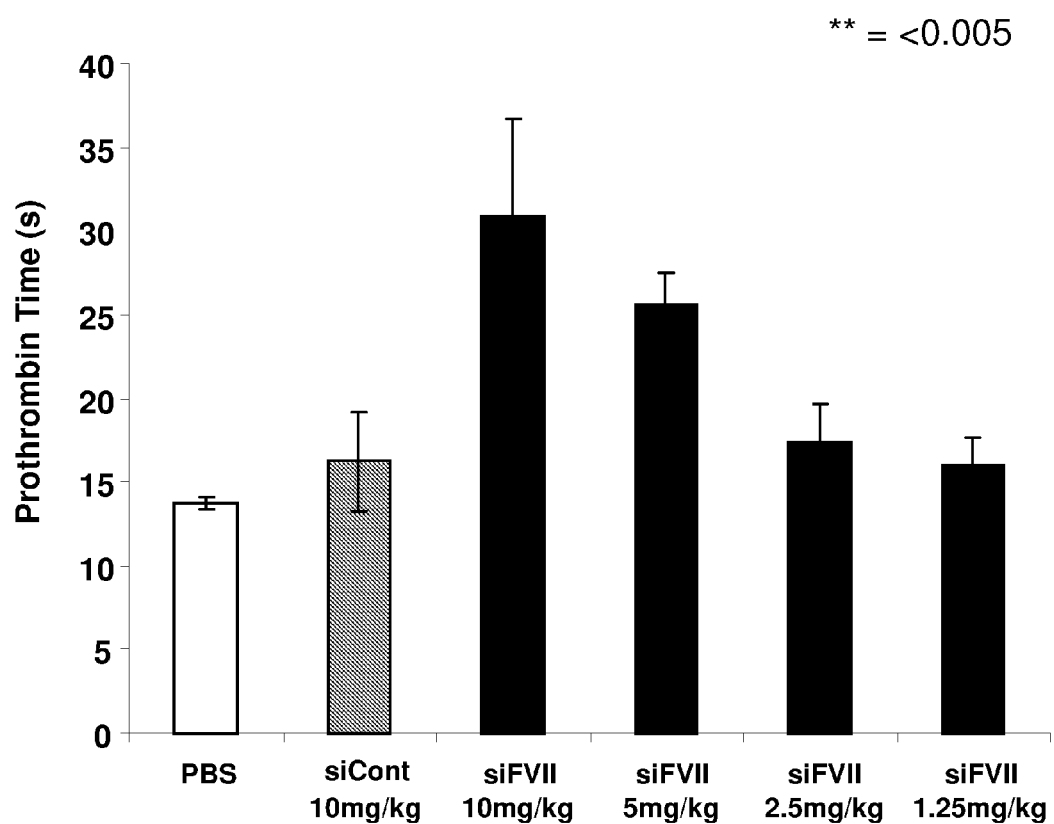
FIG. 3 is a bar graph showing prothrombin time following administration of FVII siRNA.

As would be expected, significantly reduced serum Factor VII levels produced a phenotypic effect in the treated animals. As Factor VII is part of the extrinsic coagulation pathway, treated animals had impaired clotting through this pathway as measured by prolongation in prothrombin time (PT) (FIG. 3). The phenotypic effect was found to be specific and not attributable to the delivery vehicle, as the formulated control group demonstrated no perturbations in PT. The resultant gene silencing was highly durable. Single injections of 98N12-5 formulated Factor VII-targeting siRNA (siFVII) were capable of mediating silencing persisting for nearly 4 weeks.

The sequences for the sense and antisense strands of the siRNAs are as follows.

```
siFVII:
sense:
                                    SEQ ID NO: 1
5'-GGAucAucucAAGucuuAcT*T-3' antisense:
                                    SEQ ID NO: 2
5'-GuAAGAcuuGAGAuGAuccT*T-3' siCont:
sense:
                                    SEQ ID NO: 3
5'-cuuAcGcuGAGuAcuucGAT*T-3' antisense:
                                    SEQ ID NO: 4
5'-UCGAAGuACUcAGCGuAAGT*T-3'
```

2'-O-Me modified nucleotides are in lower case, 2'-Fluoro modified nucleotides are in bold lower case, and phosphorothioate linkages are represented by asterisks. siRNAs were generated by annealing equimolar amounts of complementary sense and antisense strands.

All animal procedures used were approved by the Institutional Animal Care and Use Committee (IACUC) and were consistent with local, state, and federal regulations as applicable. C57BL/6 mice (Charles River Labs, MA) and Sprague-Dawley rats (Charles River Labs, MA) received either saline or siRNA in lipidoid formulations via tail vein injection at a volume of 0.01 mL/g. Serum levels of Factor VII protein were determined in samples collected by retroorbital bleed using a chromogenic assay (Coaset Factor VII, DiaPharma Group, OH or Biophen FVII, Aniara Corporation, OH). Liver mRNA levels of Factor VII were determined using a branched DNA assay (QuantiGene Assay, Panomics, CA).

Lipidoid-based siRNA formulations included lipidoid, cholesterol, poly(ethylene glycol)-lipid (PEG-lipid), and siRNA. Formulations were prepared using a protocol similar to that described by Semple and colleagues (Maurer et al. Biophys. J. 80:2310-2326, 2001; Semple et al., Biochim. Biophys. Acta 1510:152-166, 2001). Stock solutions of 98N12-5(1).4 HCl MW 1489, mPEG2000-Ceramide C16 (Avanti Polar Lipids) MW 2634 or mPEG2000-DMG MW 2660, and cholesterol MW 387 (Sigma-Aldrich) were prepared in ethanol and mixed to yield a molar ratio of 42:10:48. Mixed lipids were added to 125 mM sodium acetate buffer pH 5.2 to yield a solution containing 35% ethanol, resulting in spontaneous formation of empty lipidoid nanoparticles. Resulting nanoparticles were extruded through a 0.08μ membrane (2 passes). siRNA in 35% ethanol and 50 mM sodium acetate pH 5.2 was added to the nanoparticles at 1:7.5 (wt:wt) siRNA:total lipids and incubated at 37° C. for 30 min. Ethanol removal and buffer exchange of siRNA-containing lipidoid nanoparticles was achieved by tangential flow filtration against phosphate buffered saline using a 100,000 MWCO membrane. Finally, the formulation was filtered through a 0.2μ sterile filter. Particle size was determined using a Malvern Zetasizer NanoZS (Malvern, UK). siRNA content was determined by UV absorption at 260 nm and siRNA entrapment efficiency was determined by Ribogreen assay 32. Resulting particles had a mean particle diameter of approximately 50 nm, with peak width of 20 nm, and siRNA entrapment efficiency of >95%. See also PCT/US2007/080331.

TABLE 4

Abbreviations of nucleoside monomers used in nucleic acid sequence representation. It will be understood that these monomers, when present in an oligonucleotide, are mutually linked by 5'-3'-phosphodiester bonds.

| Abbreviation | Nucleoside(s) |
| --- | --- |
| A | adenosine |
| C | cytidine |
| G | guanosine |
| U | uridine |
| N | any nucleotide (G, A, C, U, or dT) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | a phosphorothioate linkage |

Example 3

Factor VII as a Target for the Treatment of Viral Hemorrhagic Fevers

Figure 4:
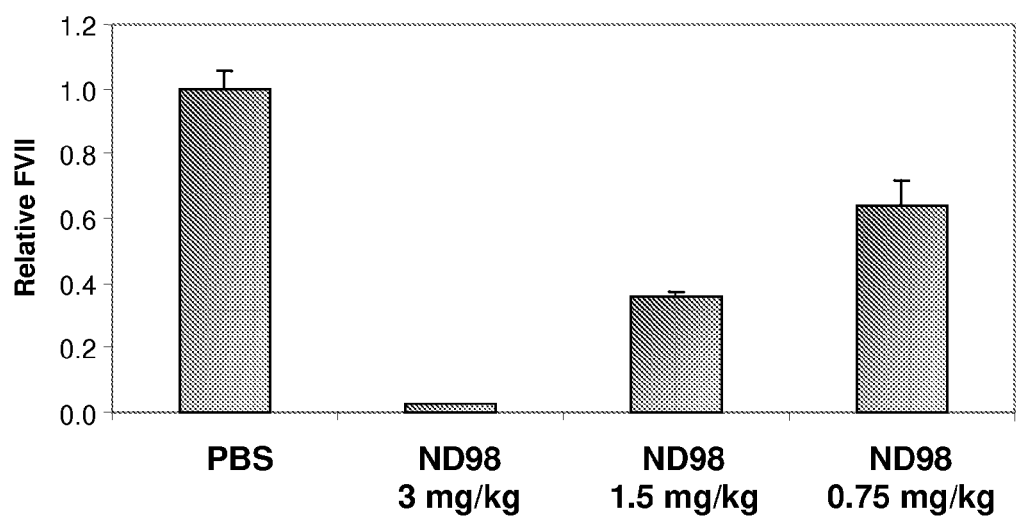
FIG. 4 is a bar graph showing FVII protein levels in mouse hepatocytes following treatment with a liposomally-formulated FVII dsRNA. A liposomally-formulated luciferase dsRNA was used as a negative control.

Robust in vivo silencing of Factor VII in hepatocytes in mice was observed following administration of a lipid-formulated FVII dsRNA (LNP-01 FVII) (FIG. 4). Mice were treated intravenously with the dsRNA, and serum was analyzed for FVII protein 24 hrs later. The decrease in FVII protein levels occurred in a dose-dependent manner. An LNP-01 formulated luciferase siRNA was used as a negative control.

Figure 5:
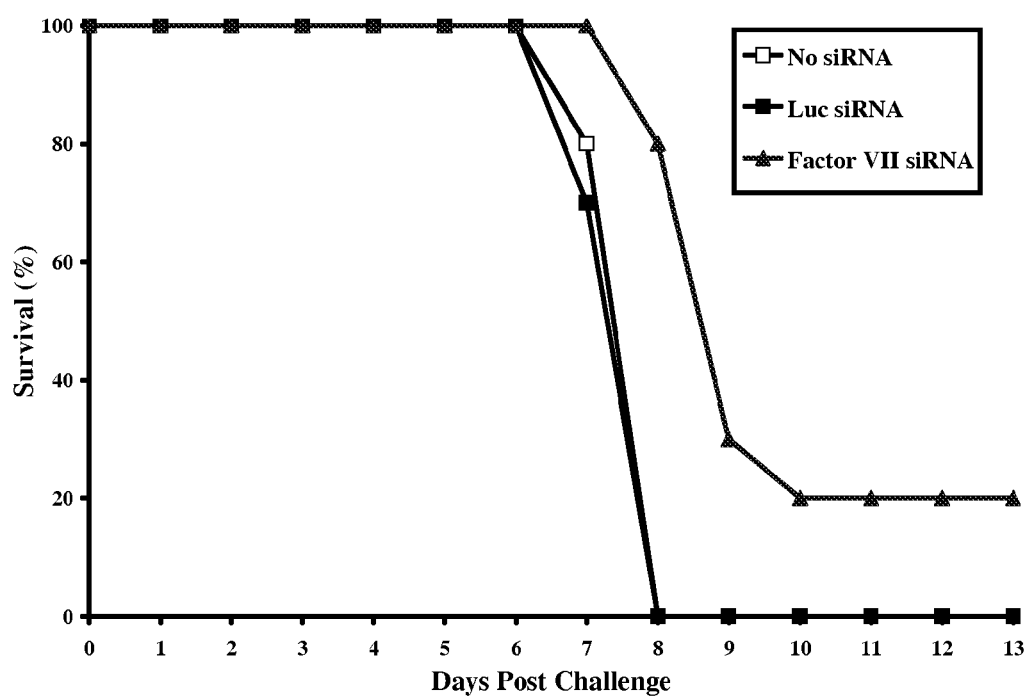
FIG. 5 is a graph showing survival levels of mice infected with Ebola, and treated with FVII dsRNA. Negative controls included untreated mice and mice treated with a luciferase dsRNA.
Figure 6:
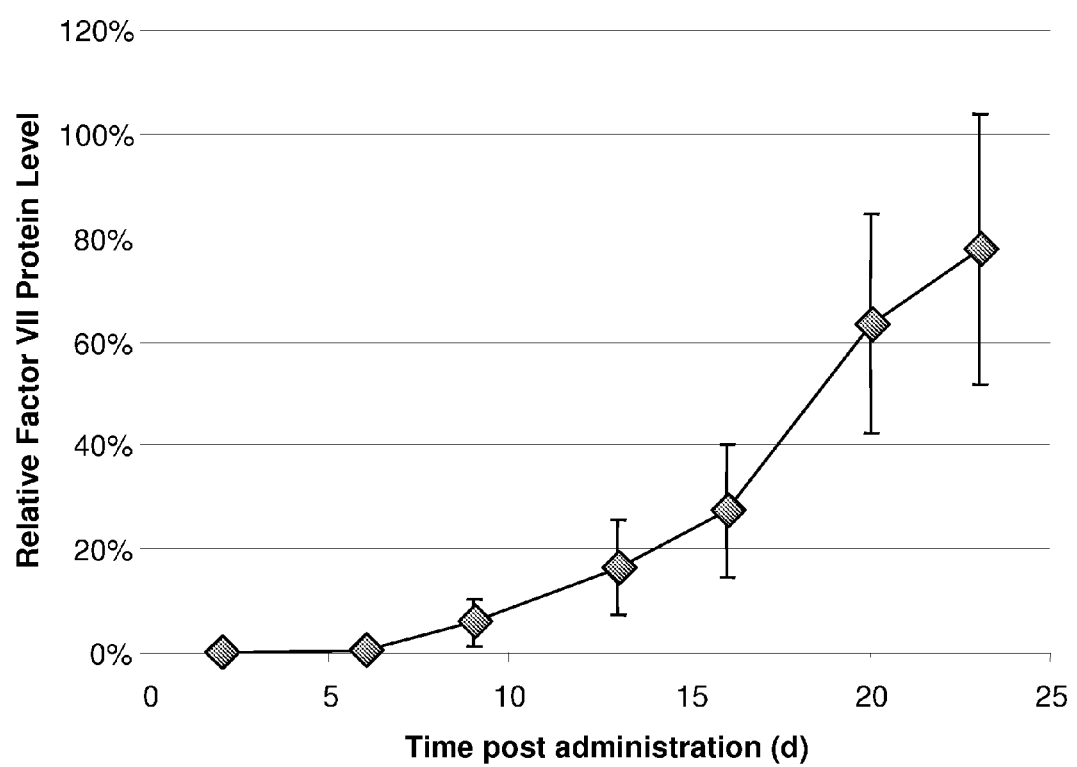
FIG. 6 is a graph showing levels of Factor VII protein over time in C57BL/6 mice treated with a single bolus i.v. injection of LNP01-siFVII at 5 mg/kg at timepoint 0.

Preliminary data using a non-optimized liposomally-formulated dsRNA to Factor VII showed a beneficial survival effect in mice infected with Ebola virus (FIG. 5). Mice were treated with LNP-01 formulated siRNA at day 0 (5 mg/kg i.v.) and at day 3 (3 mg/kg i.p.) after infection with 30,000 LD50 of Ebola-Zaire. Mice were monitored for survival with n=10 per treatment group. Negative controls included untreated mice and mice treated with LNP-01 formulated luciferase siRNA. The observed result was consistent with the benefit seen with recombinant anti-coagulant NapC2 (Geisbert et al., 2003, Lancet, 362:1953-1958) and was particularly encouraging given the reduced role for coagulopathy in the mouse model versus that seen in Ebola-infected non-human primates and humans.

Example 4

Treatment with siFVII Exhibited an Extended Effect

C57BL/6 mice were treated with a single bolus i.v. injection of LNP01-siFVII at 5 mg/kg. FIG. 6 shows that this administration caused decreased FVII levels that lasted for more than 3 weeks.

Example 5 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, UnterschleiBheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support is used for RNA synthesis. The modified solid support is prepared as follows:

Diethyl-2-azabutane-1,4-dicarboxylate AA

AA

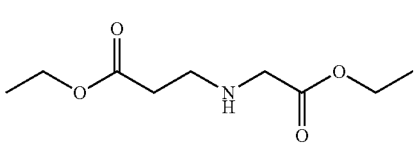

A 4.7 M aqueous solution of sodium hydroxide (50 mL) is added into a stirred, ice-cooled solution of ethyl glycinate hydrochloride (32.19 g, 0.23 mole) in water (50 mL). Then, ethyl acrylate (23.1 g, 0.23 mole) is added and the mixture is stirred at room temperature until completion of the reaction is ascertained by TLC. After 19 h the solution is partitioned with dichloromethane (3×100 mL). The organic layer is dried with anhydrous sodium sulfate, filtered and evaporated. The residue is distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

AB

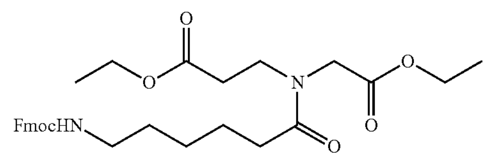

Fmoc-6-amino-hexanoic acid (9.12 g, 25.83 mmol) is dissolved in dichloromethane (50 mL) and cooled with ice. Diisopropylcarbodiimde (3.25 g, 3.99 mL, 25.83 mmol) is added to the solution at 0° C. It is then followed by the addition of Diethyl-azabutane-1,4-dicarboxylate (5 g, 24.6 mmol) and dimethylamino pyridine (0.305 g, 2.5 mmol). The solution is brought to room temperature and stirred further for 6 h. Completion of the reaction is ascertained by TLC. The reaction mixture is concentrated under vacuum and ethyl acetate is added to precipitate diisopropyl urea. The suspension is filtered. The filtrate is ished with 5% aqueous hydrochloric acid, 5% sodium bicarbonate and water. The combined organic layer is dried over sodium sulfate and concentrated to give the crude product which is purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

AC

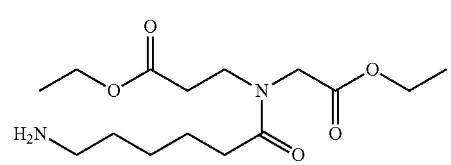

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) is dissolved in 20% piperidine in dimethylformamide at 0° C. The solution is continued stifling for 1 h. The reaction mixture is concentrated under vacuum, water is added to the residue, and the product is extracted with ethyl acetate. The crude product is purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

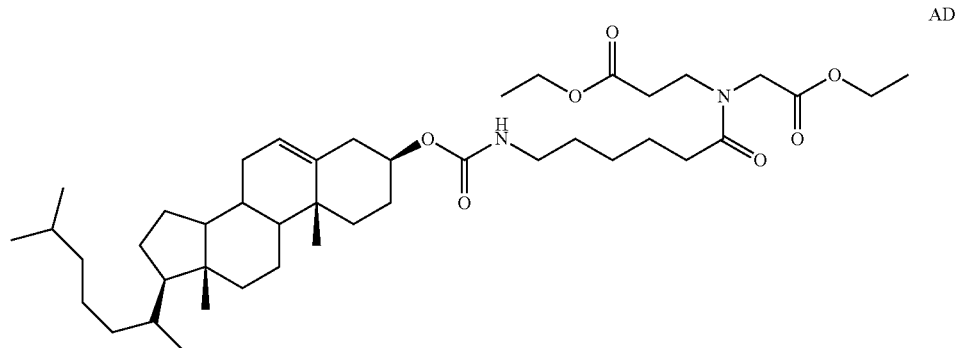

The hydrochloride salt of 3-[(6-Amino-hexanoyl)-ethoxycarbonylmethyl-amino]-propionic acid ethyl ester AC (4.7 g, 14.8 mmol) is taken up in dichloromethane. The suspension is cooled to 0° C. on ice. To the suspension diisopropylethylamine (3.87 g, 5.2 mL, 30 mmol) is added. To the resulting solution cholesteryl chloroformate (6.675 g, 14.8 mmol) is added. The reaction mixture is stirred overnight. The reaction mixture is diluted with dichloromethane and ished with 10% hydrochloric acid. The product is purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

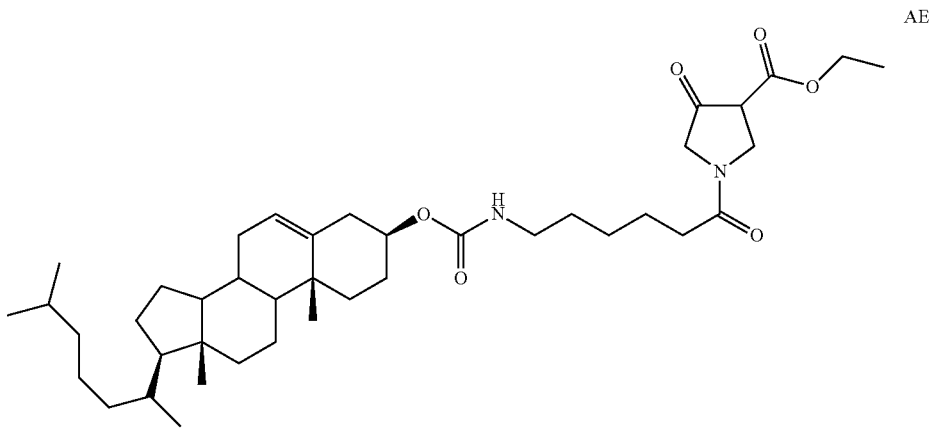

Potassium t-butoxide (1.1 g, 9.8 mmol) is slurried in 30 mL of dry toluene. The mixture is cooled to 0° C. on ice and 5 g (6.6 mmol) of diester AD is added slowly with stirring within 20 mins. The temperature is kept below 5° C. during the addition. The stirring is continued for 30 mins at 0° C. and 1 mL of glacial acetic acid is added, immediately followed by 4 g of $NaH_2PO_4 \cdot H_2O$ in 40 mL of water The resultant mixture is extracted twice with 100 mL of dichloromethane each and the combined organic extracts are ished twice with 10 mL of phosphate buffer each, dried, and evaporated to dryness. The residue is dissolved in 60 mL of toluene, cooled to 0° C. and extracted with three 50 mL portions of cold pH 9.5 carbonate buffer. The aqueous extracts are adjusted to pH 3 with phosphoric acid, and extracted with five 40 mL portions of chloroform which are combined, dried and evaporated to dryness. The residue is purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

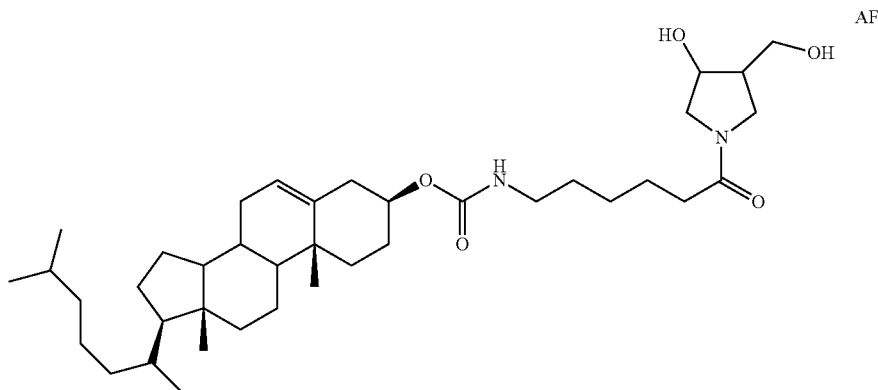

Methanol (2 mL) is added dropwise over a period of 1 h to a refluxing mixture of b-ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) is added, the mixture is extracted with ethylacetate (3×40 mL). The combined ethylacetate layer is dried over anhydrous sodium sulfate and concentrated under vacuum to yield the product which is purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

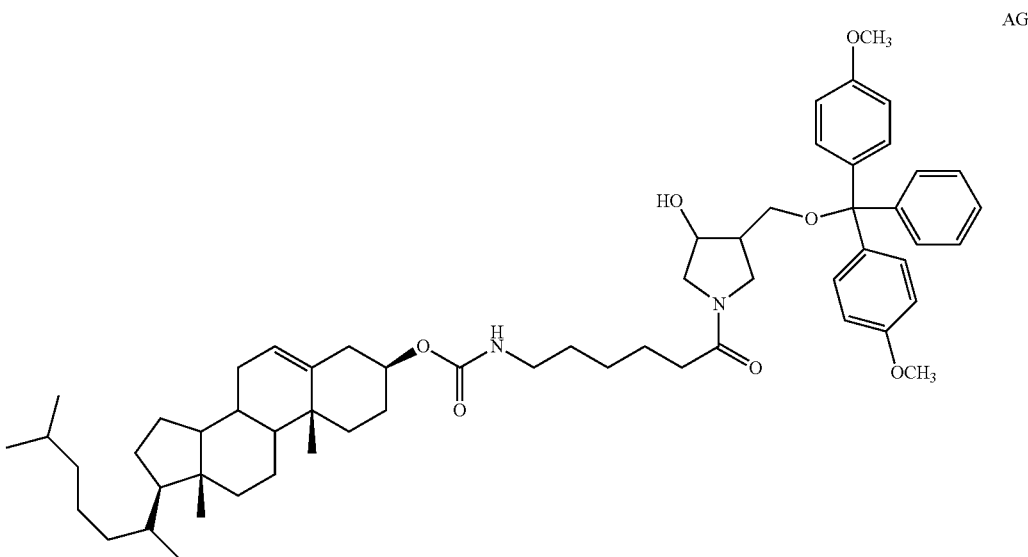

Diol AF (1.25 gm 1.994 mmol) is dried by evaporating with pyridine (2×5 mL) in vacuo. Anhydrous pyridine (10 mL) and 4,4'-dimethoxytritylchloride (0.724 g, 2.13 mmol) are added with stifling. The reaction is carried out at room temperature overnight. The reaction is quenched by the addition of methanol. The reaction mixture is concentrated under vacuum and to the residue dichloromethane (50 mL) is added. The organic layer is ished with 1M aqueous sodium bicarbonate. The organic layer is dried over anhydrous sodium sulfate, filtered and concentrated. The residual pyridine is removed by evaporating with toluene. The crude product is purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

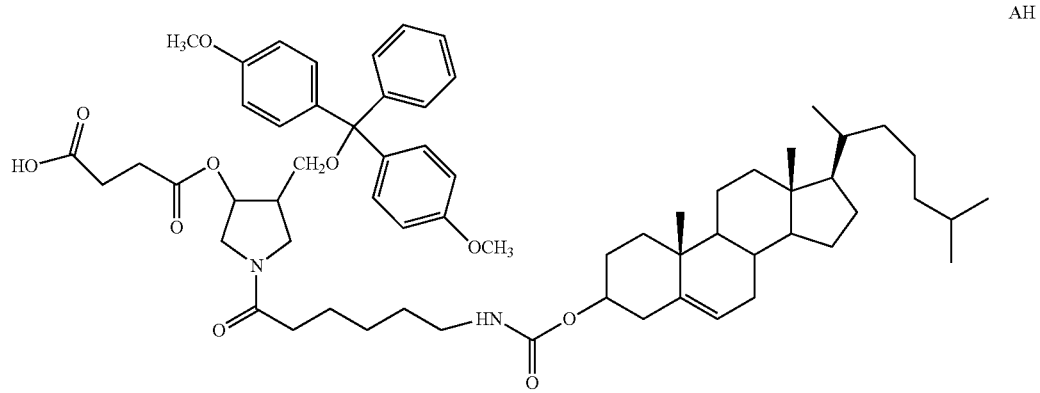

AH

Compound AG (1.0 g, 1.05 mmol) is mixed with succinic anhydride (0.150 g, 1.5 mmol) and DMAP (0.073 g, 0.6 mmol) and dried in a vacuum at 40° C. overnight. The mixture is dissolved in anhydrous dichloroethane (3 mL), triethylamine (0.318 g, 0.440 mL, 3.15 mmol) is added and the solution is stirred at room temperature under argon atmosphere for 16 h. It is then diluted with dichloromethane (40 mL) and ished with ice cold aqueous citric acid (5 wt %, 30 mL) and water (2×20 mL). The organic phase is dried over anhydrous sodium sulfate and concentrated to dryness. The residue is used as such for the next step.

Cholesterol Derivatised CPG AI

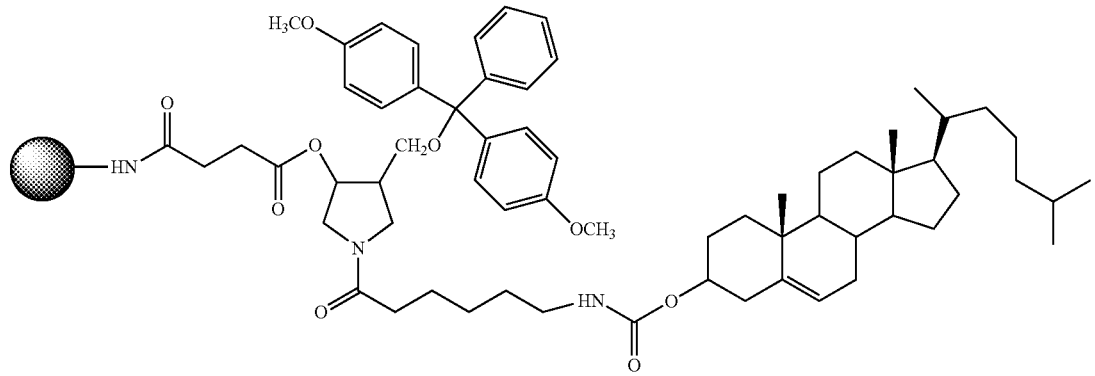

AI

Succinate AH (0.254 g, 0.242 mmol) is dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) are added successively. To the resulting solution triphenylphosphine (0.064 g, 0.242 mmol) in acetonitrile (0.6 ml) is added. The reaction mixture turned bright orange in color. The solution is agitated briefly using a wrist-action shaker (5 mins). Long chain alkyl amine-CPG (LCAA-CPG) (1.5 g, 61 mM) is added. The suspension is agitated for 2 h. The CPG is filtered through a sintered funnel and ished with acetonitrile, dichloromethane and ether successively. Unreacted amino groups are masked using acetic anhydride/pyridine. The achieved loading of the CPG is measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") is performed as described in WO 2004/065601, except that, for the cholesteryl derivative, the oxidation step is performed using the Beaucage reagent in order to introduce a phosphorothioate linkage at the 5'-end of the nucleic acid oligomer.

We claim:

1. A double-stranded ribonucleic acid (dsRNA), wherein said dsRNA comprises a sense strand and an antisense strand, wherein said sense strand and said antisense strand form a duplex structure, wherein said antisense strand comprises a region of complementarity with an mRNA encoding Factor VII, wherein said region of complementarity is less than 30 nucleotides in length, and wherein said sense strand comprises at least 15 contiguous nucleotides of the sequence of SEQ ID NO: 5.

2. The dsRNA of claim 1, wherein the sense strand comprises the sequence of SEQ ID NO:5, and the antisense strand comprises the sequence of SEQ ID NO:6.

3. The dsRNA of claim 1, wherein the dsRNA can reduce liver Factor VII mRNA levels in rats by at least 25% silencing with a single administration of a dose 98N12-5 formulated Factor VII-targeting siRNA.

4. The dsRNA of claim 1, wherein at least one nucleotide of said sense strand or said antisense strand is a modified nucleotide.

5. The dsRNA of claim 4, wherein said modified nucleotide is chosen from the group consisting of: a 2'-O-methyl modified nucleotide, a nucleotide comprising a 5'-phosphorothioate group, and a terminal nucleotide linked to a cholesteryl derivative or dodecanoic acid bisdecylamide group.

6. The dsRNA of claim 4, wherein said modified nucleotide is chosen from the group consisting of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

7. The dsRNA of claim 4, wherein said modified nucleotide comprises a phosphorothioate or a 2'-modified nucleotide.

8. The dsRNA of claim 1, wherein said duplex structure is at least 15 base pairs in length.

9. The dsRNA of claim 1, wherein said duplex structure is 19-21 base pairs in length.

10. A cell comprising the dsRNA of claim 1.

11. A pharmaceutical composition, comprising a dsRNA of claim 1 and a pharmaceutically acceptable carrier.

12. A method for inhibiting the expression of a Factor VII gene in a cell, the method comprising:
    (a) introducing into the cell a double-stranded ribonucleic acid (dsRNA) of claim 1; and
    (b) maintaining the cell produced in step (a) for a time sufficient to obtain degradation of the mRNA transcript of the Factor VII gene, thereby inhibiting expression of the Factor VII gene in the cell.

13. A method of treating or managing a viral hemorrhagic fever comprising administering to a patient in need of such treatment or management a therapeutically effective amount of a dsRNA of claim 1.

14. A vector comprising a regulatory sequence operably linked to a nucleotide sequence that encodes at least one strand of a dsRNA of claim 1.

15. A cell comprising the vector of claim 14.

16. The dsRNA of claim 1, wherein said sense strand comprises SEQ ID NO: 5.

17. The dsRNA of claim 1, wherein said antisense strand comprises SEQ ID NO: 6.

18. The dsRNA of claim 1, wherein said sense strand consists of SEQ ID NO:5.

19. The dsRNA of claim 1, wherein the antisense strand consists of SEQ ID NO:6.

20. The dsRNA of claim 1, wherein said sense strand consists of SEQ ID NO: 5 and said antisense strand consists of SEQ ID NO:6.

21. The dsRNA of claim 1, wherein said sense strand and said antisense strand are at least 19 nucleotides in length.

22. The dsRNA of claim 1, wherein each strand of said dsRNA is 21 nucleotides in length.

23. The dsRNA of claim 1, wherein at least one strand of said dsRNA has a single-stranded nucleotide overhang of 1 to 4 nucleotides.

24. The pharmaceutical composition of claim 11, wherein said sense strand comprises SEQ ID NO:5, and said antisense strand comprises SEQ ID NO:6.

25. The vector of claim 14, wherein said sense strand comprises SEQ ID NO:5, and said antisense strand comprises SEQ ID NO:6.

* * * * *